(12) United States Patent
Shizukuishi

(10) Patent No.: US 9,943,275 B2
(45) Date of Patent: Apr. 17, 2018

(54) IMAGING APPARATUS

(71) Applicant: Makoto Shizukuishi, Sendai (JP)

(72) Inventor: Makoto Shizukuishi, Sendai (JP)

( * ) Notice: Subject to any disclaimer, the term of this patent is extended or adjusted under 35 U.S.C. 154(b) by 61 days.

(21) Appl. No.: 14/963,568

(22) Filed: Dec. 9, 2015

(65) Prior Publication Data

US 2016/0157791 A1 Jun. 9, 2016

(30) Foreign Application Priority Data

Dec. 9, 2014 (JP) .................................. 2014-248934
Oct. 1, 2015 (JP) .................................. 2015-195851

(51) Int. Cl.
*A61B 6/00* (2006.01)
*A61B 6/03* (2006.01)

(52) U.S. Cl.
CPC ............ *A61B 6/4435* (2013.01); *A61B 6/032* (2013.01); *A61B 6/4028* (2013.01); *A61B 6/4233* (2013.01); *A61B 6/4275* (2013.01); *A61B 6/4417* (2013.01); *A61B 6/508* (2013.01)

(58) Field of Classification Search
CPC ....... A61B 6/025; A61B 6/4233; A61B 6/032; A61B 6/4266; A61B 6/06; A61B 6/00; G01N 23/08; G01T 1/17
USPC ................. 378/21, 22, 25, 26, 189
See application file for complete search history.

(56) References Cited

U.S. PATENT DOCUMENTS

| | | | |
|---|---|---|---|
| 4,937,453 A | 6/1990 | Nelson | |
| 5,175,754 A | 12/1992 | Casey et al. | |
| 5,434,417 A | 7/1995 | Nygren | |
| 5,552,596 A | 9/1996 | Ravetto et al. | |
| 5,821,540 A | 10/1998 | Sato et al. | |
| 9,658,348 B2 * | 5/2017 | Sung | ........................ H04N 5/32 |
| 2002/0017609 A1 | 2/2002 | Danielsson | |
| 2002/0018543 A1 | 2/2002 | Danielsson | |

(Continued)

FOREIGN PATENT DOCUMENTS

| | | | |
|---|---|---|---|
| JP | 07333348 A | 12/1995 |
| JP | H11347023 A | 12/1999 |

(Continued)

*Primary Examiner* — Don Wong

(74) *Attorney, Agent, or Firm* — Harness, Dickey & Pierce, P.L.C.

(57) ABSTRACT

A tomographic imaging system includes a source configured to irradiate an object; a first image sensor including a first semiconductor substrate having a first face upon which a monolithic first pixel array is located; and a gantry configured to hold the first image sensor and rotate the image sensor around the object about a first rotation axis, the first pixel array including a first plurality of pixels configured to receive light that travels through or from the object based on the irradiation, the first plurality of pixels of the first pixel array being arranged in one or more rows and a plurality of columns such that, a total number of the one or more rows is less than a total number of the plurality of columns, and the one or more rows extend in a first direction, the first image sensor being arranged such that an angle between the first direction and a second direction is greater than 45 degrees and equal to or less than 90 degrees, the second direction being a direction parallel to the rotation axis or a direction in which the object moves during analysis of the object by the imaging system.

15 Claims, 11 Drawing Sheets

(56) References Cited

U.S. PATENT DOCUMENTS

| | | |
|---|---|---|
| 2004/0251419 A1 | 12/2004 | Nelson et al. |
| 2006/0005681 A1 | 1/2006 | Lambert et al. |
| 2010/0204942 A1 | 8/2010 | Danielsson et al. |
| 2014/0334601 A1 | 11/2014 | Shizukuishi |

FOREIGN PATENT DOCUMENTS

| | | |
|---|---|---|
| JP | 2005-106644 A | 4/2005 |
| JP | 2006-300662 A | 11/2006 |
| JP | 2007-078369 A | 3/2007 |

* cited by examiner

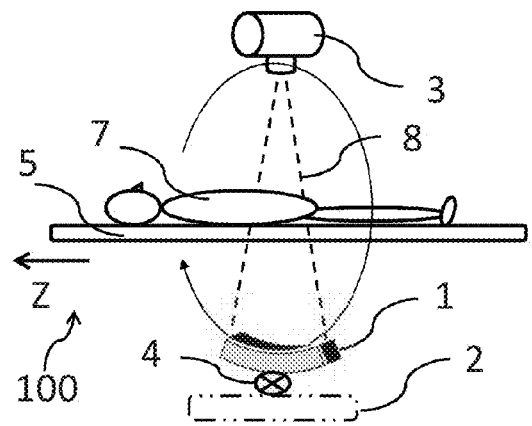
*Fig.1 (a) Prior Art*
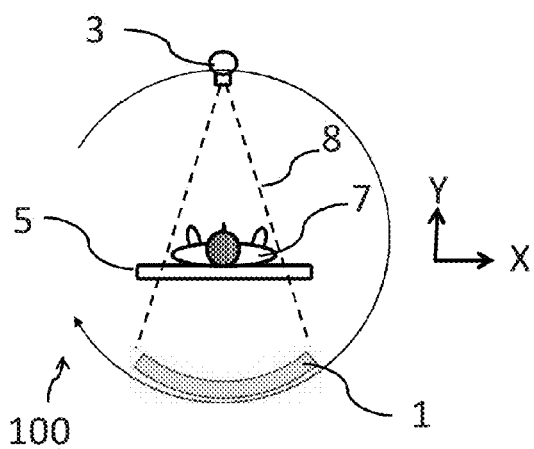
*Fig.1 (b) Prior Art*
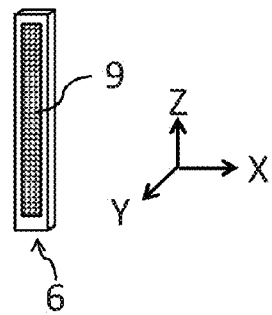
*Fig.1 (c) Prior Art*
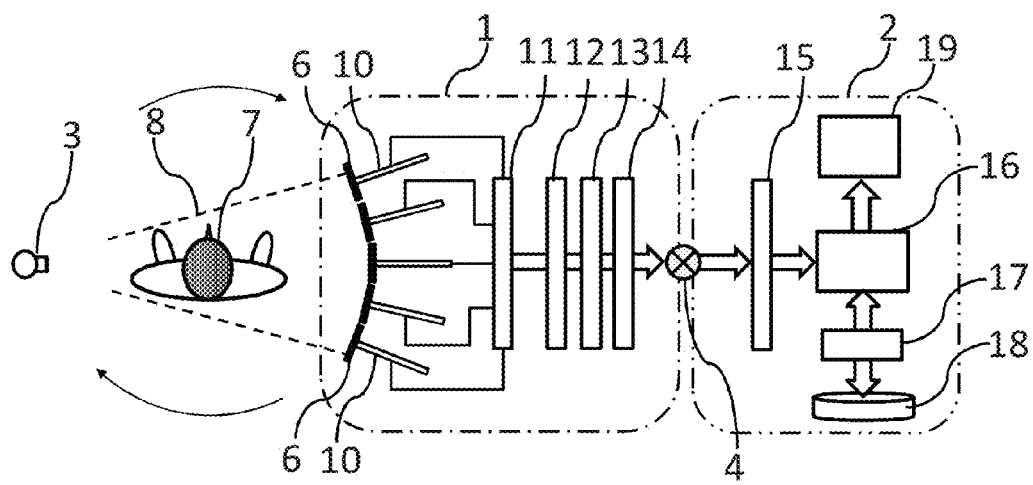
*Fig.1 (d) Prior Art*

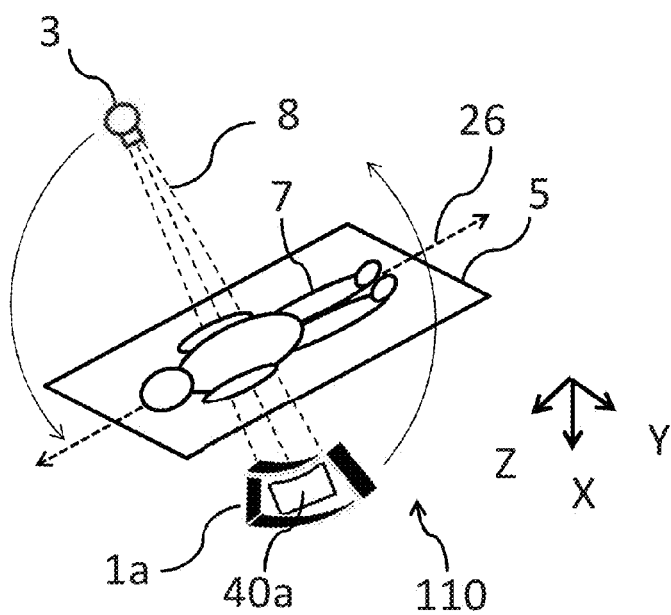
*Fig.2 (a)*
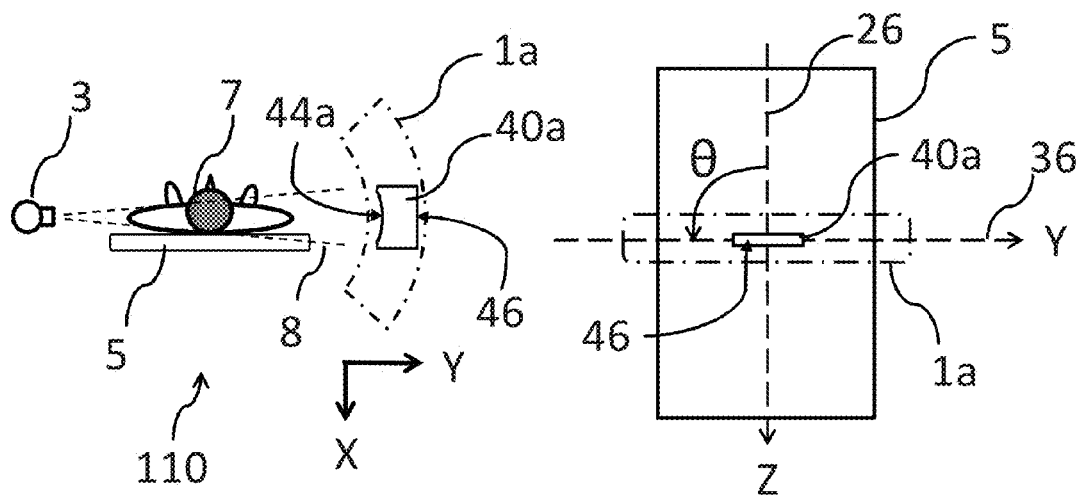
*Fig.2 (b)*     *Fig.2 (c)*

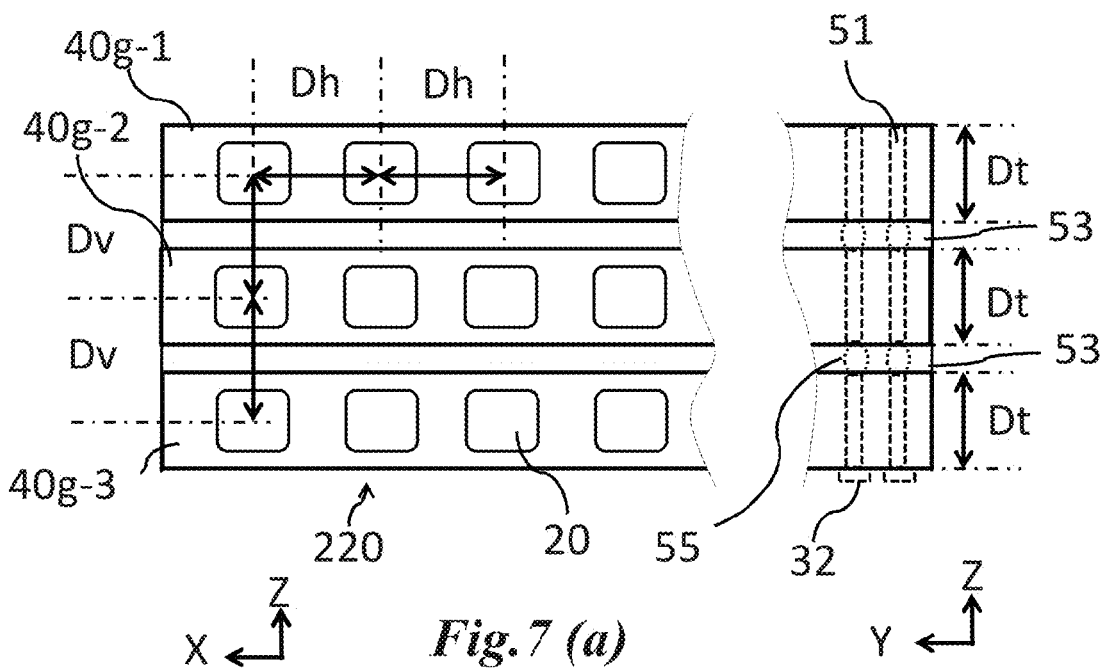
*Fig.7 (a)*
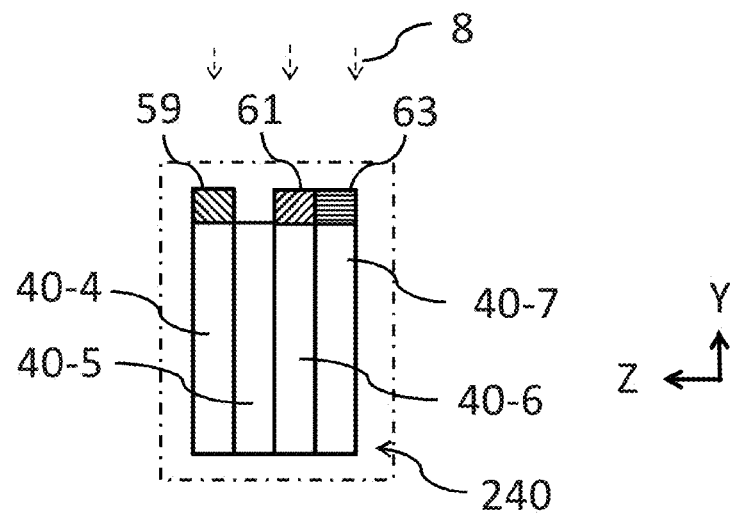
*Fig.7 (b)*
*Fig.7 (c)*

IMAGING APPARATUS

CROSS-REFERENCE TO RELATED APPLICATION

This application claims priority under 35 U.S.C. § 119 to Japanese Patent Application No. 2015-195851 filed on Oct. 1, 2015, in the Japanese Patent Office (JPO), and Japanese Patent Application No. 2014-248934 filed on Dec. 9, 2014, in the JPO, the entire contents of each of which are incorporated herein by reference.

BACKGROUND

1. Technical Field

Example embodiments relate to an imaging apparatus such as computed tomography enabling high spatial, timing and energy resolution with smaller form factor and lower power consumption.

2. Related Art

A computed tomographic (CT) system or, a CT system is now widely used for medical imaging and diagnostics. FIG. 1(a) shows a conventional CT system 100. The CT system 100 includes an imaging unit 1 including a set of sensor elements and data acquisition systems (DAS), an X-ray source 3, and a bed 5 on which an imaged object or patient 7 lies down. The X-ray source 3 projects an X-ray beam 8, for example, through the object 7 to be detected by sensor elements inside the imaging unit 1. The imaging unit 1 and the X-ray source 3 are located in an opposite position inside their housing called a gantry. The imaging unit 1 and the X-ray source 3 rotate around the object 7 taking a slice image, and the object 7 on the bed 5 is moved in a direction of Z-axis to get additional slice images. As shown in FIGS. 1(a), 1(b) and 1(c), a Cartesian coordinate system is defined. The X-ray source 3 and the imaging unit 1 rotate on the X-Y plane, and the bed 5 and/or the object 7 moves in a direction of Z-axis which is perpendicular to the X-Y plane. The CT system 100 also includes an image processing unit 2 which performs a reconstruction of a slice image. Electrical communication between the imaging unit 1 and the image processing unit 2 is performed by a slip-ring 4. Image data obtained by the imaging unit 1 is transferred to a network interface circuit 15 in the image processing unit 2 through the slip-ring 4. A central processing unit (CPU) 16, a disk controller circuit 17, and a memory disk unit 18 reconstruct a slice image, which is displayed on an image output device 19. Moreover, a cooling system and a regulated power supply system (not illustrated), for example, should be equipped with a CT system.

Consequently, such a CT system becomes heavy, large sized and expensive machinery, which may be suitable mainly to large scale hospitals in metropolises, and less suitable for healthcare providers with smaller facilities.

SUMMARY

At least some example embodiments provide a computed tomographic (CT) system that enables the discovery of a disease or other condition harmful to the health of a patient in the early stages of the condition thereby reducing medical expenses.

As shown in FIGS. 1(c) and 1(d), the conventional CT system 100 uses plural elongated (e.g., long and/or slender) area image sensors 6, on each of which a two dimensional pixel array 9 is formed. These image sensors 6 are mounted in the imaging unit 1 such that the longer direction of the image sensor 6 is parallel to the direction of the Z-axis around the object 7, and each pixel array 9 is opposed to a fan beam X-ray source 3. The pixel array 9, however, has a flat surface formed on a silicon substrate, and it may be difficult or, alternatively, impossible to have a smooth curved surface to oppose a fan beam X-ray in the direction of the rotation in the X-Y plane. Further, with an increase in the pixel or slice number of the image sensor 6 in the direction of Z-axis, the cone angle of X-ray also increases, which may degrade image quality due to an artifact caused by the X-ray attenuations with different incident X-ray angles to the flat surface of the pixel array 9.

Sensitivity variations between the image sensors 6 or between the pixels are desirably reduced, or alternatively, minimized in the rotating direction of the imaging unit 1 on the X-Y plane, because the worst sensor or pixel limits dominate the overall system sensitivity and reconstructed image quality. Otherwise, it may be difficult to reduce total X-ray dose, especially human exposure. As shown in FIGS. 1(d), the plural image sensors 6 and multi-channel analog-to-digital convertor (ADC) circuit boards 10 of CT system 100 should be fixed firmly being opposed to the X-ray source 3 inside the imaging unit 1. It should be also noted that the imaging unit 1 moves around the object, and it may be necessary to replace parts like the image sensors 6 with a new parts, regularly. With the above-referenced use environment and maintenance requirements, it may be necessary to fix the positions of each image sensor 6 and each multi-channel ADC circuit board 10 with a high degree of accuracy in such a manner that each image sensor 6 and each multi-channel ADC circuit board 10 are still removable by precision machining tools, when replacement is necessary, in order to maintain an initial reconstructed image quality. As a result, efforts for downsizing, weight reduction and cost reduction of the CT system 100 may all be made more difficult by the above-referenced precision tools, in addition to other significant factors associated with at least some conventional systems like the CT system 100 including, for example, a large installation space, heavy maintenance loads, a large-scale regulated power supply, and a large-scale cooling system of the conventional CT system 100.

Further, from an electrical point of view, peripheral circuits and input or output terminals which will not detect incident light (e.g., elements other than the pixel array 9 on the image sensor 6) may be damaged by radiation, and thus, an area for such peripheral circuits and input or output terminals should be reduced or minimized. In at least some conventional systems like the CT system 100, vertical and horizontal scanning circuits, and input and output terminals besides the pixel array 9 are integrated on the image sensor 6 in order to reduce a blind or dead area on the image sensor 6. As a result, the pixel array 9 is located close to the chip side edges which are not flat or smooth, and have a lot of crystal defects due to a wafer dicing process. Accordingly, the location of the pixel array 9 may affect the image quality because the photo-diodes and peripheral circuits are formed close to these edges, and thus, may be exposed to incoming contaminations of metal impurities or reactive chemicals, for example.

A high speed multi-channel analog-to-digital convertor (ADC) with a 16 bit or higher resolution as a semiconductor discrete part, for example, is mounted on a print circuit board 10 which is attached to the backside of the image sensor 6. As shown in FIGS. 1(d), input and output signals to or from the print circuit board 10 are connected to a later-stage signal processing circuit block, which includes a signal control circuit 11, a multiplexer circuit 12, a data buffer circuit 13 and a parallel to serial converter circuit 14. In at least some conventional systems, a high speed line driver is needed between each print circuit board 10 and the later-stage signal processing circuit block, because of the long wiring length. Consequently, even more power consumption or heat generation may be caused around the DAS.

Further, regarding the reliability and the maintenance on at least some conventional systems like the CT system 100, a semiconductor chip of the conventional CT system 100 may be damaged by high energy radiation like X-rays, for example. As for the Metal-Oxide-Semiconductor (MOS) device, charges trapped in a gate insulator of silicon dioxide (SiO2), for example, may cause threshold voltage shift in a MOS transistor. This shift in threshold voltage may deteriorate image quality obtained by either MOS type or CCD type image sensors, and eventually reduce a product life time. A scintillator, for example, a columnar crystal Cesium Iodide, is applied above the conventional image sensor to convert the X-ray to visible light, which is effectively absorbed by a silicon substrate within ten (10) micron meters in depth. The columnar crystal Cesium Iodide is, however, a deliquescent substance and needs an ambient humidity and temperature control. As a result, at least some conventional systems like CT system 100 require periodic or regular maintenance including, for example, image sensor replacements and sensitivity adjustments.

Besides sensitivity or lower X-ray dose and image quality, other functionalities of a CT system should be considered. These other functionalities of the CT system that should be considered include, for example, a higher data transfer rate with lower power consumption, a smaller or portable form factor, a reduced maintenance load, and a reduction of the influence of surroundings like temperature, humidity and mechanical vibrations should be considered. For example, it may be desirable for a CT system to provide high spatial, time and energy resolution in order to enable three dimensional (3D) imaging with a variety of valuable bio-medical information even from active or moving objects, for example.

Further, as is discussed above, a conventional CT system uses a number of detector elements arranged around and facing an object where the detector elements have very specific positioning and angles with respect to each other. As a result, a conventional CT system may become a system composed of heavy, large-sized and extremely expensive machinery. However, it may be desirable to reduce or solve such difficulties or inconveniences in order to create a CT system that is affordable and portable for medical professionals, and thus, useful all over the world including in developing countries.

According to at least one example embodiment of the CT system, an image sensor which is installed inside an imaging unit is mounted on the same plane as a slice image of an object, and the semiconductor surface of the image sensor, where integrated circuits are formed, is at angle of 45 to 90 degrees to the direction of a bed or an object to be moved, and at least one face of the semiconductor substrate of the image sensor faces an object and receives an incident light, the incident light being, for example, X-rays that travel through or from the object. With such a configuration, a CT system may be implemented with reduced size, lighter weight, parts that are easier to replace, and less influence from environmental factors like temperature, humidity and mechanical vibrations, in comparison to a conventional CT system.

According to at least one example embodiment of the CT system, the face of the semiconductor substrate of the image sensor, which receives an incident light or X-ray, may be concave in shape. With such a configuration, incident beam angle dependence on the X-ray beam attenuation, which may cause a false or alias image referred to as an artifact, is reduced or prevented.

According to at least one example embodiment of the CT system, the imaging unit may use plural image sensors inside an imaging unit around an object. With an increase in the number of the image sensor used in the imaging unit, an X-ray source may project a wider fan beam angle, and a larger number of transmitted X-ray signals can detected simultaneously in a short time. As a result of such an arrangement, a total dose of X-rays received by an object being analyzed by the CT system may be reduced.

According to at least one example embodiment of the CT system, the concave face of the semiconductor substrate of the image sensor is covered by a thin silicon dioxide layer. With such a configuration, crystal defects caused by a mechanical or a thermal stress may be reduced and contamination of the semiconductor substrate by incoming metal impurities or reactive chemicals may be prevented.

According to at least one example embodiment of the CT system, the image sensor chip has a circular hollow inside the chip, where the inside and outside substrate sides (e.g., faces) are covered by a thin silicon dioxide layer. According to at least one example embodiment, the image sensor may have a donut shape. With such a configuration, all or, alternatively, substantially all of the photo-diodes and peripheral circuits of an image sensor chip are formed in a single die on the same plane, which may result in a sensitivity of the image sensor chip to variations around the object being reduced or, alternatively, minimized. The CT system using the single die image sensor can be smaller in size than a conventional CT system and portable.

According to at least one example embodiment of the CT system, an imaging unit may include plural image sensors which are stacked in the direction perpendicular to a slice image of an object. With such a configuration, a pixel number or so-called slice number can be increased.

According to at least one example embodiment of the CT system, the distance between adjacent pixels in a horizontal direction may be equal to the distance between adjacent pixels in a vertical direction. According to at least one example embodiment, the horizontal distance may be larger than the semiconductor substrate thickness. With such a configuration, a high spatial resolution with an accuracy of, for example, 0.1 micron meter or less can be realized.

According to at least one example embodiment of the CT system, the stacked image sensor includes a metal optical shield between the image sensors. For example, according to at least one example embodiment, a metal optical shield may include heavier metal atoms like tungsten or lead in order to attenuate unexpected incident light with wrong directions or scattered X-ray beams. With such a configuration, even higher image qualities may be achieved relative to a conventional CT system due to less cross-talk noise and fewer artifacts.

According to at least one example embodiment of the CT system, a color filter, or near infrared filter is laminated on the concave face of the image sensor used in the stacked image sensor. With such a configuration, the image quality of the CT system is improved and the CT system has a hybrid imaging capabilities which enable multi-diagnoses using different energy X-rays and/or near infrared (NIR) of multiple wavelengths. According to at least one example embodiment, a scintillator film is laminated on the concave face of the image sensor used in the stacked image sensor.

With such a configuration, X-rays that pass through the scintillator without emitting a light may also be detected by the image sensor.

According to at least one example embodiment of the CT system, the image sensor is placed along the trace of a helix extending in the direction perpendicular to the slice image of an object. According to at least one example embodiment, more than two image sensors are located approximately along the helix. With such a configuration, the CT system according to at least one example embodiment may have advantageous effects of both helical and multi-scan systems.

According to at least one example embodiment of the CT system, the image sensor has a slit, which makes it easy to deform the substrate of the image sensor such that a sidewall of the substrate faces the helix. According to at least one example embodiment, two or more image sensors with slits are stacked by a holding member having a screw thread inside. With such a configuration, the image sensor or image sensor module including multiple image sensors stacked on each other may be accurately fixed helically inside the imaging unit.

According to at least one example embodiment of the CT system, the photo-diodes on the silicon substrate extend radially toward the incident light beam around the object. With such a configuration, sensitivity dependence on the incident light or X-ray angle may be reduced or, alternatively, minimized.

According to at least one example embodiment of the CT system, the peripheral circuits including the analog-to-digital converters (ADCs) and other CMOS circuits are integrated on a same image sensor chip. With such a configuration, high speed signal processing and lower device temperature due to reduced clock frequencies and lower power consumptions may be achieved.

According to at least one example embodiment of the CT system, on chip buffer memory and a data compression circuit are integrated on the image sensor. With such a configuration, the image data after analog to digital conversion is compressed down to, for example, between one third ($1/3$) and one fifth ($1/5$) without data loss, and thus the data transfer bit rate may be also decreased.

According to at least one example embodiment of the CT system, an image processing chip is stacked on the top of the image sensor. With such a configuration, compressed image data obtained from the image sensor is sent directly to the upper image processing chip with a reduced or, alternatively, minimum number of electrical paths by through silicon vias (TSVs), which results in higher speed data transfer and a data processing with lower power consumption relative to a conventional CT system.

BRIEF DESCRIPTION OF THE DRAWINGS

The above and other features and advantages of example embodiments will become more apparent by describing in detail example embodiments with reference to the attached drawings. The accompanying drawings are intended to depict example embodiments and should not be interpreted to limit the intended scope of the claims. The accompanying drawings are not to be considered as drawn to scale unless explicitly noted.

FIG. 1(a) is a diagram illustrating a perspective view of a conventional computed tomographic (CT) system.

FIG. 1(b) is a diagram illustrating a plan view of a conventional CT system with a view direction parallel to the Z-axis as illustrated in FIG. 1(a).

FIG. 1(c) is a diagram illustrating a perspective view of a conventional image sensor used in a conventional CT system.

FIG. 1(d) is a diagram illustrating a plan view of an imaging unit and an image processing unit used in a conventional CT system.

FIG. 2(a) is a diagram illustrating a perspective view of a CT system according to at least one example embodiment.

FIG. 2(b) is a diagram illustrating a plan view of a CT system with a view direction parallel to the Z-axis as illustrated in FIG. 2(a) according to at least one example embodiment.

FIG. 2(c) is a diagram illustrating a plan view of an arrangement of an image sensor in an imaging unit from a view point above the CT system 110 (i.e., looking down upon the bed 5) and a view direction parallel to the X-axis according to at least one example embodiment.

FIG. 7(a) is a diagram illustrating a side view of an image sensor module used in the CT system with a view direction parallel to the Y-axis, and a view direction parallel to the X-axis, according to at least one example embodiment.

FIG. 7(b) is a diagram illustrating a side view of an image sensor module used in the CT system with a view direction parallel to a direction of a beam of light incident on the image sensor module according to at least one example embodiment.

FIG. 7(c) is a diagram illustrating a side view of an image sensor module used in the CT system with a view direction parallel to the X-axis according to at least one example embodiment.

DETAILED DESCRIPTION OF EXAMPLE EMBODIMENTS

Figure 3:
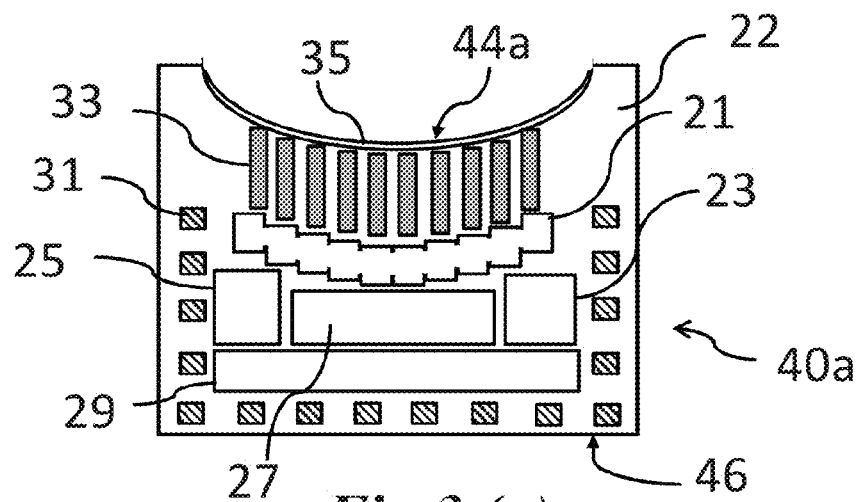
FIG. 3(a) is a diagram illustrating a plan view and a block diagram of an image sensor used in the CT system according to at least one example embodiment.
FIG. 3(b) is a diagram illustrating a plan view of an arrangement of an image sensor in an imaging unit from a top side of the CT system according to at least one example embodiment with a view direction parallel to the X-axis.
FIG. 3(c) is a diagram illustrating an example of tracks of scanned images made by moving an image sensor around an object according to at least one example embodiment.
Figure 3:
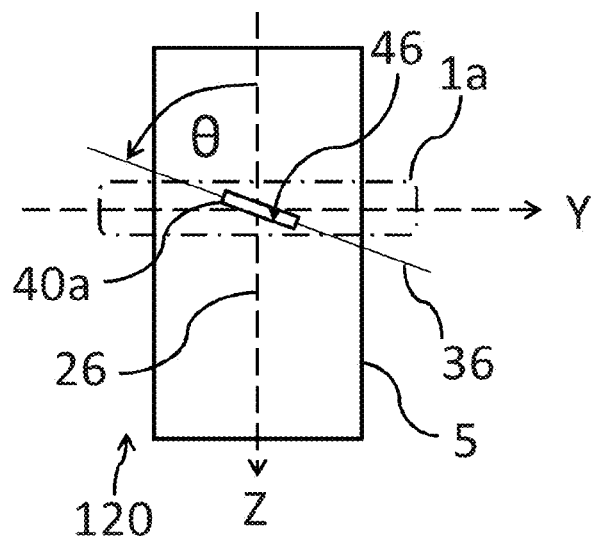
Figure 3:
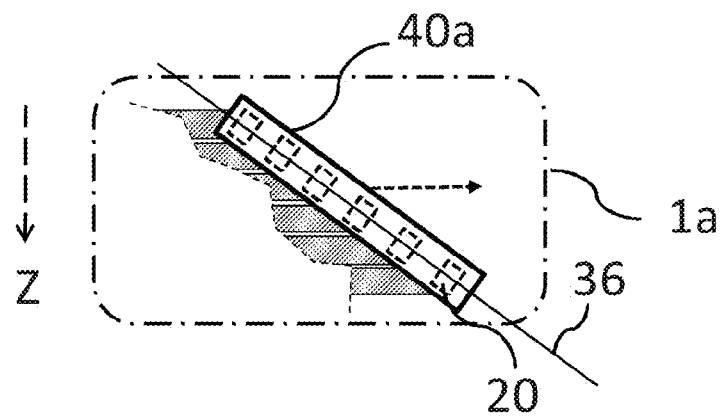

Detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected to", "coupled to", or "on" another element, it may be directly connected to, directly coupled to, or directly on the other element, or intervening elements may be present. In contrast, when an element is referred to as being "directly connected to", "directly coupled to", or "directly on" another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments. As used herein, the singular forms "a", an and the are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof. It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

FIG. 2(a) is a diagram illustrating a perspective view of a computed tomographic (CT) system 110, which includes an imaging unit 1a in which an image sensor 40a is installed. A CT system includes an X-ray source 3, and a bed 5 on which an imaged object or patient 7 lies down. The X-ray source 3 projects an X-ray beam 8, for example, through the object 7 to be detected by the image sensor 40a. X-ray beam 8 may be collimated to form a defined fan beam angle by a collimator (not illustrated), for example. The imaging unit 1a and the X-ray source 3 are located in opposing positions inside a housing called a gantry (not illustrated). According to at least some example embodiments, the X-ray source 3 and imaging unit 1a may be diametrically opposed to each other with respect to a diameter that passes through the object 7. The imaging unit 1a and the X-ray source 3 rotate around the object 7 taking a slice image about a rotation axis 26, and the object 7 on the bed is moved to get additional slice images in a direction of the Z-axis illustrated in FIG. 2(a). In the example shown in FIG. 2(a), the rotation axis 26 is parallel to the Z-axis. The CT system 110 may also include an image processing unit (an example of which is explained in greater detail below with reference to at least FIGS. 10(b) and 10(c)) which performs a reconstruction of a slice image. As shown in FIG. 2(a), a Cartesian coordinate system is defined. As shown in FIG. 2(b), according to at least one example embodiment, the X-ray source 3 and the image sensor 40a may rotate on the X-Y plane, and the bed 5 and/or the object 7 may move in a direction of Z-axis which is perpendicular to the X-Y plane. A semiconductor surface of the image sensor 40a where integrated circuits are formed may also be perpendicular to the Z axis. One face of the image sensor 40a faces an object 7 in order to detect X-ray beam 8, which is incident on the face of the image sensor 40a that faces the object 7. For example, according to at least some example embodiments, the image sensor 40a is placed at an angle theta (θ) of 90 degrees to the Z-axis, as shown in FIG. 2(c). In the case of the conventional CT system, the conventional area image sensor is placed at an angle theta (θ) of zero degree to the Z-axis. For example, in the example illustrated in FIGS. 2(b), a plan view of the image sensor 40a includes a long face 46 and a concave face 44a that opposes the long face 46. FIG. 2(c) shows the long face 46 of the image sensor 40a. As in shown in FIG. 2(c), the long face 46 may be rectangular in shape, and thus, may have two parallel short sides and two parallel long sides. As is shown in FIG. 2(c), according to at least one example embodiment, the image sensor 40a may be arranged such that a first line 36 is perpendicular to the Z-axis. For the purpose of simplicity, the first line 36 is illustrated in the present disclosure as a line that passes through a center of the long face 46 and is parallel to the long sides of the first face 46. However, as will be discussed in further detail below with reference to FIG. 3(c), the first line 36 is a reference line that indicates a direction in which one or more rows of pixels 20 extend along a face of an image sensor that upon which X-ray beams 8 are incident (e.g., the concave face 44a for sensor 40a).

For the purpose of simplicity, the term "X-ray source" is used in the present disclosure in the description of several example embodiments. However, according to at least some example embodiments, elements described in the present disclosure as X-ray sources may be embodied sources capable of providing other types of radiation instead of, or in addition to, X-rays including, but not limited to, gamma rays and near infrared (NIR) light).

As is discussed in greater detail below, the concave face 44a of the image sensor 40a used in at least some example embodiments is exposed to incident X-ray beams 8, thus allowing X-ray beams 8 to be incident on the photodiodes 33 of the pixels 20, for example, after the X-ray beams pass through or emerge from an object being analyzed (e.g., the object 7). With a narrow fan beam angle or a pencil beam, the face exposed to the X-ray beams 8 could be flat in shape. However, according to at least one example embodiment, as shown in FIGS. 2(a) and 2(b), the concave face 44a may be concave in shape, and thus, angles of beams that are incident on the concave face 44a may become even or equal in length. With such a configuration, incident beam angle dependence on the X-ray beam attenuation, which may cause false or alias images (e.g., artifacts), is reduced or, alternatively, prevented. Unlike the conventional arrangement of a number of image sensors with mechanical constructions around the object, no mechanical and angle alignment with high accuracy is required. For example, because the exposed surfaces of the individual sensors 6 of the conventional CT system 100 illustrated in FIGS. 1(a)-(d) are flat, the sensors 6 each need to be arranged with precise angles relative to the X-ray source 3 when being installed into the CT system 100 initially or as replacements. To the contrary, the size of the image sensor 40a and the curvature of the concave face 44a may be controlled and determined, instead, prior to installation of the image sensor 40a in a CT system, during the image sensor manufacturing process, which may include a photo-lithography step. Thus, the process of installing one or more image sensors 40a in a CT system initially or as replacements may be substantially simplified relative to the process of installing the sensors 6. The CT system, using the image sensor 40a with the exposed concave face 44a and the arrangement, described herein, of the concave face 44a relative to an object being analyzed (e.g., the object 7), may realize a small or portable form factor, relatively low weight, relatively easy parts replacement, relatively low maintenance load, and a relatively low amount of influence by environmental factors including, for example, temperature, humidity and mechanical vibrations, as a result of the limited number of parts and mechanical constructions used.

FIG. 3(a) shows a plan view and a block diagram of the image sensor 40a used in the CT system according to at least one example embodiment. On the image sensor 40a, a plurality of photo-diodes 33, input or output terminals 31, and peripheral circuits are formed. As used in the present disclosure, the term peripheral circuits may refer to, for example, a signal read-out and scanning circuit 21, a timing pulse generator circuit 23, an analog-to-digital converter (ADC) circuit 25, a digital signal processing circuit 27, and/or an interface circuit 29. According to at least some example embodiments, the plurality of photo-diodes 33, input or output terminals 31, and peripheral circuits are formed on a single die, a single chip, or formed as a single-die image sensor chip.

According to at least some example embodiments, the peripheral circuits may be formed at locations on the semiconductor substrate 22 of the image sensor 40a that are spaced away (i.e., separated) from edges of the image sensor 40a. For example, as is illustrated in FIG. 3(a), peripheral circuits (e.g., the signal read-out and scanning circuit 21, the timing pulse generator circuit 23, the analog-to-digital converter (ADC) circuit 25, the digital signal processing circuit 27, and the interface circuit 29) are separated from edges of the image sensor 40a (i.e., edges of the semiconductor substrate 22) by input or output terminals 31.

Each photo-diode from among the plurality of photo-diodes 33 may be a part of a corresponding pixel circuit 20. Pixel circuits 20 are also referred to, in the present disclosure, as pixels 20, and will be discussed in greater detail below with reference to FIG. 3(c). According to at least some example embodiments, the concave face 44a of the image sensor 40a (illustrated in FIG. 3(a) as a concave upper side of the plan-view of the image sensor 40a), may be covered by a thin silicon dioxide layer 35. The silicon dioxide layer 35 may reduce crystal defects caused by a mechanical or a thermal stress, and may protect the portions of the image sensor under the silicon dioxide layer 35 from contaminants like, for example, metal impurities or reactive chemicals. Each photo-diode 33 extends inside the same silicon substrate 22 to the signal read-out and scanning circuit 21 (with a length of, for example, 5 to 500 microns ($\mu m$)) to detect infrared light or X-ray beams of less than 50 kiloelectronvolts (Kev) where photo-electric effect is dominant, for example. Longer lengths like 500 $\mu m$ to 10 mm photo-diodes may be used for detecting X-ray energy of 50 Kev or higher where Compton scattering is dominant, for example. A thin silicon dioxide layer (e.g., layer 35) is discussed with reference to a number of embodiments in the present disclosure. According to at least some example embodiments, with respect to the thin silicon dioxide layer (e.g., layer 35) discussed in the present disclosure, the thickness of the thin silicon dioxide layer may be in the range of, for example, 100 angstroms (A) (i.e., 0.01 microns) to 10 microns ($\mu m$). According to at least some example embodiments, it may be desirable for the thickness of the thin silicon dioxide layer (e.g., layer 35) discussed in the present disclosure to be in the range of, for example, 1000 (A) to 1 ($\mu m$), for example. Depending on the film growing speed, thinner layers (e.g., films) less than 1000 (A) may be prepared by a thermal oxidation of silicon, which, in at least some cases, may be a relatively slow process. Further, thicker layers (e.g., films) more than 1000 (A) (i.e., 0.1 microns) may be prepared by chemical vapor deposition (CVD), for example, which, in at least some cases, may be a relatively fast process. According to at least some example embodiments, the thin silicon dioxide layer (e.g., layer 35) discussed in the present disclosure can be formed by a combination of the two above-referenced processes by, for example, growing a thin thermally grown silicon dioxide layer first, and adding and/or stacking the thick CVD silicon dioxide layer on the first layer (i.e., the thin thermally grown silicon dioxide layer).

For the purpose of simplicity, the term "silicon substrate" is used in the present disclosure in the description of several example embodiments. However, according to at least some example embodiments, elements described in the present disclosure as silicon substrates may alternatively be embodied by substrates composed of semiconductor materials other than (or, alternatively, in addition to) silicon.

According to at least some example embodiments, sensor architectures used to implement the pixels (e.g., pixels 20), photo-diodes (e.g., photo-diodes 33) and/or scanning circuits (e.g., scanning circuits 21) described in the present disclosure may follow, for example, known charged coupled device (CCD)-type sensor architectures or metal oxide semiconductor (MOS)-type sensor architectures.

With such a configuration, either light (i.e., electromagnetic radiation) with longer wavelengths like infrared light or light with shorter wavelengths like X-ray beams can be effectively detected by a single crystalline silicon substrate without using toxic or chemically unstable materials like amorphous selenium (a-Se), cadmium telluride (Cd—Te), or a needle crystalline cesium iodide (Cs—I) scintillator. In addition, peripheral circuits like AD convertors and other CMOS circuits can be integrated on a same image sensor chip, which enables high speed signal processing and lower device temperature due to reduced clock frequencies and lower power consumptions. Further, sensitivity variations or other non-uniformities in pixel characteristics, for example, can be reduced or, alternatively, minimized because all the pixels, being in line along the revolutions around the object, may be prepared on the same chip. Still further, some or all peripheral circuits in the image sensor 40a may be formed away from the face upon which the X-ray beams are incident (e.g., the concave face 44a) and most of X-rays may be adsorbed or generate photo-carriers in the photo-diodes 33. As a result, radiation damage in MOS elements of the image sensor 40a (e.g., MOS field-effect transistors (MOSFETS)) or white defective spots on reproduced images generated by the image sensor 40a may be reduced. Further, a product life time of the image sensor 40a and/or a CT system including the image sensor 40a may be extended, and a maintenance frequency of the image sensor 40a and/or a CT system including the image sensor 40a may be decreased.

FIG. 3(b) is a plan view of an arrangement of an image sensor 40a in an imaging unit 1a with a view direction parallel to the X-axis from a view point above the CT system 120 (i.e., looking down upon the bed 5) according to at least one example embodiment. The CT system 120 may have the same structure and operation as the CT system 110, with the following exceptions. The image sensor 40a is placed in the imaging unit 1a at a tilt angle theta ($\theta$), which is less than 90 degrees but larger than 45 degrees (45<$\theta$<90) to the Z-axis. For example, as is shown in FIG. 3(b), the image sensor 40a may be arranged such that the tilt angle theta ($\theta$) exists between the rotation axis 26 (illustrated in FIG. 3(b) the Z-axis) and the first line 36. According to at least some example embodiments, the image sensor 40a may include an array of pixels 20 arranged into a plurality of columns and one or more rows such that the number of rows in the array of pixels 20 is less than the number of columns in the array of pixels 20. For example, in FIG. 3(c), the array of pixels 20 is arranged in six columns and one row. Further, as is illustrated in FIG. 3(c) and discussed above with respect to FIG. 2(c), the first line 36 indicates a direction in which the one or more rows of the array of pixels 20 extend (i.e., the first line 36 is parallel to a direction in which the one or more rows of the array of pixels 20 extend). Thus, as is shown in FIG. 3(b), the image sensor 40a may be arranged such that the tilt angle theta ($\theta$) exists between the Z-axis and the first line 36 (i.e., such that the tilt angle theta ($\theta$) exists between the rotation axis 26 and a direction in which the one or more rows of the array of pixels 20 extend).

Further, according to at least some example embodiments, the image sensor 40a may be arranged such that the tilt angle theta ($\theta$) exists between a direction in which the object 7 and or bed 5 moves (illustrated in FIGS. 3(b) and 3(c) as the Z-axis) and the first line 36.

Though, for the purpose of simplicity, the array of pixels 20 in FIG. 3(c) is illustrated as having only six columns and one row of pixels, according to at least some example embodiments, the array of pixels 20 may have any number of pixels arranged in any number of columns and any number of rows that is less than the number of columns. Further, the array of pixels 20 may be formed monolithically on a single semiconductor chip.

As is shown in FIG. 3(c), when the image sensor is tilted in the manner shown in FIG. 3(b), the paths of pixels 20 (illustrated in FIG. 3(c) as bars extending from the pixels 20) do not overlap as the image sensor 40a moves around an object in the CT system 120, and thus pixels 20 of a single image sensor 40a may follow, respectively, different paths simultaneously as the image sensor 40a rotates around an object by analyzed by the CT system 120. As is noted above, each pixel 20 may include a corresponding photodiode from among the plurality of photodiodes 33. According to at least some example embodiments, the tracks or traces (i.e., paths) of the pixels 20 may become helical shape during continuous image capturing when an object being analyzed by the CT system 120 moves in the direction of Z-axis. According to at least example embodiments, by changing the tilt angle theta ($\theta$) between 45 and 90 degrees, spatial resolution of the image reproduced by the CT system 120 and correlation between the neighboring pixels can be set to a desirable level or, alternatively, optimized in accordance with the nature of the object. According to at least some example embodiments, the tilt angle theta ($\theta$) may be changed between 45 and 90 degrees in accordance with the desires of a user and/or manufacturer of the CT system 120. According to at least some example embodiments, the space or distance between the pixels 20 (e.g., a pitch of the pixels 20) is determined not by the mechanical assembly but the photomask design and semiconductor device manufacturing process capable of performing highly accurate alignment even for distances less than 0.1 micron-meter ($\mu$m), for example.

FIG. 4(a) is a diagram illustrating a plan view of a CT system 130 with respect to view direction parallel to the Z-axis, which includes an imaging unit 1b, an X-ray source 3, a bed 5 on which an imaged object or patient 7 lies down. The X-ray source 3 projects an X-ray fan beam 8, for example, through the object 7 to be detected by the imaging unit 1b. The imaging unit 1b uses three image sensors 40b-1, 40b-2 and 40b-3, for example, which encircle the imaged object 7. Similar to image sensor 4a, each image sensor 40b-1-40b-3 has a concave face. According to at least some example embodiments, for each of image sensors 40b-1-40b-3, the surface of the concave face is parallel to the view direction of FIG. 4(a), and is covered by a thin silicon dioxide layer (not shown in this figure). For each of image sensors 40b-1-40b-3, the curved (i.e., concave) face of the sensor, which is exposed to the incident fan beam 8, may form a part of a circumference around an object being analyzed by the CT system 130. According to at least one example embodiment, each of the image sensors 40b may have the same structure and operation as that described above with reference to the image sensor 40a, with the exception that the curvature of the concave faces of at least some of the image sensors 40b may differ from the curvature of the concave face 44a of the image sensor 40a, as is illustrated in FIG. 4(a).

With the configuration described above with reference to FIG. 4(a), which includes increasing the number of the image sensors used in the imaging unit 1b relative to, for example, imaging unit 1a of CT system 110, in addition to the above advantageous effects, an X-ray source 3 projecting a wider fan beam angle may be used to detect a larger number of transmitted X-ray signals simultaneously in a short time. Consequently, the total dose of an X-ray received by a patient may be reduced. The size of each image sensor 40b may depend on the size of a silicon wafer used; however, as explained above, the plural image sensors 40b placed in the imaging unit 1b may cover a wider field of vision in the X-Y plane. The plural image sensors 40b placed in the imaging unit 1b may be manufactured from the same silicon wafer or the same process lot, which may result limited non-uniformities of pixel characteristics such as sensitivity variations among the image sensors 40b. As explained above, peripheral circuits like AD convertors and other CMOS circuits can be integrated on each chip with a relatively small, or alternatively, minimum wiring length, which may result in reduced clock frequencies and lower power consumption in addition to higher speed signal processing and a higher signal to noise ratio (S/N) relative to, for example, at least some conventional CT systems.

FIG. 4(b) is a diagram illustrating a plan view of a CT system 140 with a view direction parallel to the Z-axis. A donut shaped imaging unit 1c includes image sensors 40c, which surround the object 7 covering 360 degrees. Each image sensor 40c has a concave face to form a circular form. The concave face, the surface of which is parallel to the view direction of FIG. 4(b), is covered by a thin silicon dioxide layer (not shown in this figure). In the example illustrated in FIG. 4(b), a movable X-ray source 3 is not used but a donut shaped target ring may be placed near the imaging unit 1c, for example. An example of a CT system including a target ring will now be discussed in greater detail with reference to FIG. 4(c). FIG. 4(c) is a diagram illustrating a perspective view of a CT system 140. The CT system 140 includes an electron beam gun 3a, a focusing and deflection coil 3b, and the imaging system 1c. The imaging system 1c includes the image sensor 40c and a target ring 3d which, according to at least some example embodiments, may arranged near, or alternatively, adjacent to the image sensor 40c in the imaging unit 1c, as is illustrated in FIG. 4(c). As is illustrated in FIG. 4(c), according to at least some example embodiments, the electron beam gun 3a generates an electron beam 3c, which is focused and deflected by a focusing and deflection coil 3b towards the target ring 3d, such that the electron beam 3c is incident on the target ring 3d. As is also illustrated in FIG. 4(c), as a result of electron beam scanning (e.g., using electron beam 3c) and a high energy electron bombardment to the target ring 3d, X-ray beams 8 are generated. X-ray beams 8 may travel through the object 7, and can be detected by the image sensor 40c located at a side of the object 7 opposite to a side of the object 7 upon which each of X-ray beams 8 are incident. Returning to FIG. 40(b), as is illustrated in FIG. 4(b), X-ray beams 8 may be incident on several different sides of the object 7. According to at least some example embodiments, some or all of image sensors 40c may be implemented by the image sensor 40a illustrated in FIG. 3(a). According to at least some example embodiments, as is discussed in greater detail below, the sensors 40(c) may include photo-diodes (not shown in this figure) that are formed inside the silicon substrate of the sensors 40(c) radially from the center of an X-ray or a gamma-ray, for example. For example, according to at least some example embodiments, some or all of image sensors 40c may be implemented by the image sensor 40m, which will be discussed in greater detail below with reference to FIG. 10(a). In addition, all the sides of the image sensors 40c may be concave in shape forming a circle around the object 7, where incident beam angles on each concave side may become even or nearly equal. As a result, incident beam angle dependence on the X-ray beam attenuation, which may cause false or alias images (e.g., artifacts), may be reduced or effectively suppressed by an error correction algorithm, for example.

With the above-referenced configuration described with reference to FIGS. 4(b) and 4(c), in addition to the above advantageous effects, an imaging unit 1c and an X-ray source like the target ring 3d are fixed inside a gantry without mechanically moving parts, which enables the CT system 140 to have a structure that omits a slip ring, and thus, allows the CT system 140 to have downsized smaller size and a higher time-resolution, relative to at least some conventional CT systems. With the CT system 140 according to example embodiments, even higher speed 3D imaging for moving organs such as a beating heart called a cardiac angiography, may be realized. Further, additional example applications disclosed herein include, but are not limited to, a positron emission tomography (PET), a single photon emission CT (SPECT) using radioactive materials (e.g., radio isotopes (RI) or positron nuclide), and an optical topography using near-infrared (NIR) light source. In the case of PET apparatus, image sensors 40c placed all around the object so as to detect two photons generated when a positron is pair-annihilated with electrons by collapse of a radioactive isotope which doses test objects. Unlike a conventional CT system using X-ray source, according to the additional example applications, even higher time and space resolutions enable the detection of the temporally brief and microscopic phenomena of a positron or a single photon emission.

FIG. 5(a) is a diagram illustrating a plan view of a single silicon die (i.e., chip) image sensor 40d being shaped so as to form a circular hole (e.g., a cylindrical opening) inside the die, thereby exposing a curved face 44d within the silicon substrate of the die such that the curved face 44d defines the circular hole and has the shape of an interior curved surface of a hollow right cylinder. According to at least some example embodiments, the curved face 44d is covered by a thin silicon dioxide layer 35 which may reduce crystal defects caused by a mechanical or a thermal stress, and may prevent contaminations from incoming metal impurities or reactive chemicals. As is illustrated in FIG. 5(a), the external shape of the die of the image sensor 40d may be a rectangle. The four edges of the rectangular exterior of the image sensor 40d may not be flat or smooth, and may have a lot of crystal defects due to a wafer dicing process, which may not affect the image quality of images generated based on the image sensor 40d because, as will be discussed in greater detail below, the photo-diodes and peripheral circuits of the image sensor 40d may be formed away from the above-referenced four edges. An object or a patient (not shown in this figure) may be placed inside the hollow formed in the die of the image sensor 40d (i.e., inside an interior of the cylindrical shape formed by the curved face 44d such that the curved face 44d encircles the object of patient). An X-ray beam that travels through an object or a patient being analyzed, or a gamma-ray from the nuclides inside dosed into the object or the patient, for example, may be detected by the circularly arrayed photo-diodes 33. The circularly arrayed photo-diodes 33 are formed inside the silicon substrate of the die of the image sensor 40d radially from the center of the circle. For example, according to at least some example embodiments, each photo-diode 33 of the image sensor 40d may be formed radially in the image sensor 40d so as to extend from the curved face 44d into the image sensor 40d in a direction parallel to a straight line between a center of the cylindrical opening and the photo-diode 33. In the same manner discussed above with reference to FIGS. 3(a) and 3(c), the plurality of photo-diodes 33 of the image sensor 40d may be included in a plurality of corresponding pixel circuits 20 (not illustrated in FIG. 5(a)), respectively, so as to form a monolithic array of pixels 20 configured to receive light that travels through or from an object located in a central portion of the cylindrical opening at the center of the image sensor 40d. In addition, the curved surface 44d may be viewed as being concave in shape and encircling the object 7, where incident beam angles on each concave side may become even or nearly equal in length. On the peripheral region of the die of the image sensor 40d, a signal read-out and scanning circuit 21, a timing pulse generator circuit 23, an AD convertor circuit 25, a digital signal processing circuit 27, and an interface circuit 29 are formed. Input or output terminals 32, in the image sensor 40d, are micro pads formed above one or more through -silicon via(s) (TSVs) which may be referred to herein as TSV structure. As is discussed in greater detail below, multiple image sensor 40d may be stacked on each other successively to increase the number of pixels in a direction parallel to the view direction of FIG. 5(a) (i.e., a direction parallel to the Z-axis). Electrical connections between multiple image sensors 40d stacked on each other may be accomplished by the TSV structure with wiring lengths that are minimized or, alternatively, reduced with respect to at least some conventional CT systems, unlike image sensors mounted in at least some conventional CT systems where each image sensor is electrically connected by a large number of long metal wirings between image sensors and supporting circuits on each print-circuit board (PCB) of the convention CT systems. According to at least one example embodiment, the image sensor 40d may be included in an imaging unit of a CT system in a manner that is the same as (or similar to) that discussed above with respect to the circularly-arranged image sensors 40c included in the imaging unit 1c of CT system 140 illustrated in FIG. 4(c). For example, according to at least some example embodiments, a CT system including the image sensor 40d may include the electron beam gun 3a, focusing and deflection coil 3b, and target ring 3d, each of which may have the same arrangement and operation as those discussed above with respect to FIG. 4(c). Accordingly, X-rays beams generated as a result of an electron beam (e.g., electron beam 3c) irradiating the target ring 3d may be incident on an object located in the hollow center of the image sensor 40d, and resulting light that passes through or from the object may be incident on pixels 20 located on the curved face 44d of the image sensor 40d.

The die size of the die of the image sensor 40d or the diameter of the circular hollow inside the die of the image sensor 40d may depend on the size of a silicon wafer being used to create the die, which is rectangular. Using a twelve inch silicon wafer, the length of a diagonal line between a first corner of the rectangular die and a second corner of the rectangular die that as cater-corner to the first corner may be less than twelve inches, and then the diameter of the circular hollow may be six to seven inches, for example. With such a configuration, in addition to the above advantageous effects, all the photo-diodes and peripheral circuits are formed in a single die which may reduce, or alternatively, minimize its sensitivity variations, signal delay times and power consumption or the die temperature. The CT system using the single die image sensor 40d, according to the embodiment, can be relatively small and portable, and may be suitable for applications like analyzing smaller objects like a part of a body or breast, performing diagnoses for small animals, or industrial uses like a three dimensional (3D) scanner that provides 3D image data to a 3D printer, for example. A cross sectional view taken along a dotted line A-A' illustrated on the image sensor 40d in FIG. 5(a) is explained below, with reference to FIG. 9(a).

FIG. 5(b) is a diagram illustrating a plan view of a single silicon die (chip) image sensor 40e having a donut shape, such that the silicon substrate of the die has a curved outer surface 43e and a curved inner surface 44e, each of which is covered by a thin silicon dioxide layer 35. The thin silicon dioxide layer 35 may reduce crystal defects caused by a mechanical or a thermal stress, and prevent contamination by incoming metal impurities or reactive chemicals. Like the image sensor 40d of FIG. 5(a), the image sensor 40e of FIG. 5(b) may include photo-diodes 33 arranged in a circular array. In the same manner discussed above with reference to image sensor 40(d) of FIG. 5(a), the plurality of photo-diodes 33 of the image sensor 40e may be included in a plurality of corresponding pixel circuits 20 (not illustrated in FIG. 5(b)), respectively. Further, the photo-diodes 33 may be formed radially in the same manner discussed above with respect to image sensor 40d of FIG. 5(a). Unlike the image sensor 40d shown in FIG. 5(a), the external shape of the die of the image sensor 40e is circular and covered by a thin silicon dioxide layer 35. Further, input or output terminals 32 and peripheral circuits including, for example, a signal read-out and scanning circuit 21, a timing pulse generator circuit 23, an AD convertor circuit 25, a digital signal processing circuit 27, and an interface circuit 29, are formed close to the outer edge.

Using a twelve inch silicon wafer, for example, the outer diameter of the donut shape may be less than twelve inches but the inner diameter of the donut shape may be more than ten inches. With such a configuration, in addition to the above advantageous effects, a CT system including the image sensor 40e, according to at least some example embodiments, can be relatively small and portable, and may be suitable for applications like dental tomography and brain topography, analysis of smaller objects like a part of a body or breast, diagnoses for small animals, or industrial use like a three dimensional (3D) scanner that provides 3D image data to a 3D printer, for example. According to at least one example embodiment, the image sensor 40e may be included in an imaging unit of a CT system in a manner that is the same as (or similar to) that discussed above with respect to the circularly-arranged image sensors 40c included in the imaging unit 1c of CT system 140 illustrated in FIG. 4(c). For example, according to at least some example embodiments, a CT system including the image sensor 40e may include the electron beam gun 3a, focusing and deflection coil 3b, and target ring 3d, each of which may have the same arrangement and operation as those discussed above with respect to FIG. 4(c). Accordingly, X-rays beams generated as a result of an electron beam (e.g., electron beam 3c) irradiating the target ring 3d may be incident on an object located in the hollow center of the image sensor 40e, and resulting light that passes through or from the object may be incident on pixels 20 located on the curved face 44e of the image sensor 40e.

Figure 6:
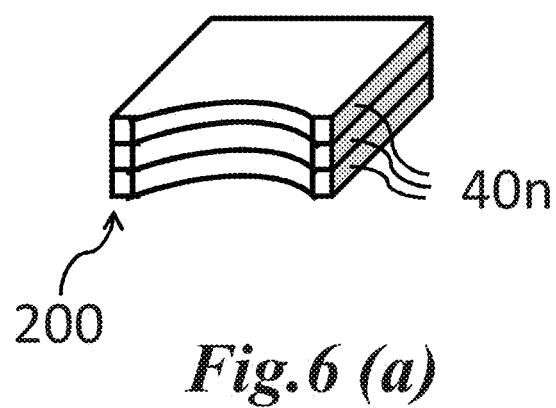
FIG. 6(a) is a diagram illustrating a perspective view of an image sensor module used in the CT system according to at least one example embodiment.
FIG. 6(b) is a diagram illustrating a perspective view of an image sensor module used in the CT system according to at least one example embodiment.
Figure 6:
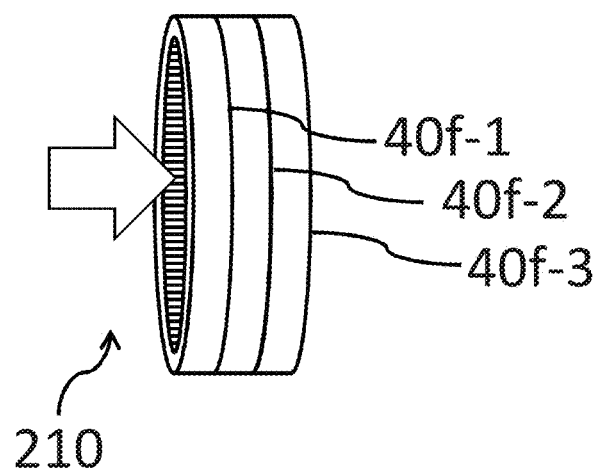

FIG. 6(*a*) is a diagram illustrating a perspective view of a sensor module 200 which includes three image sensors 40*n* stacked on each other, for example. Electrical communications between the dies of the image sensors 40*n* may be achieved, for example, by TSV structures. According to at least some example embodiments, some or all of the stacked image sensors 40*n* of the sensor module 200 may be implemented by image sensors having the structure of the image sensor 40*a* illustrated in FIG. 3(*a*) and/or image sensors having the structure of the image sensor 40*m*, which will be discussed in greater detail below with reference to FIG. 10(*a*). As is illustrated if FIG. 6(*a*), the image sensor 40*n* may be stacked in such a manner as to form a concave face of the image sensor module 200. The concave face of the image sensor module 200 may face an object to detect incident X-ray beams that pass through the object and are incident on the concave face. The plural image sensors 40*n* may be stacked in a direction parallel to the Z-axis in the CT system (e.g., a direction in which a patient or object being analyzed by the CT system is moved during analysis in a CT system), according to at least some example embodiments. With the configuration described above with reference to FIG. 6(*a*), in addition to the above advantageous effects, a pixel number or so-called a slice number can be increased, which may be useful for implementing a multi-slice CT system or cone beam type CT system with a small form factor, a high image quality, and a high speed image recognition, for example. According to at least some example embodiments, image sensor module 220 described in greater detail below with reference to FIG. 7(*a*) is an example of the manner in which image sensors 40*n* of the image sensor module 200 may be stacked.

FIG. 6(*b*) is a diagram illustrating a perspective view of an image sensor module 210, where three image sensors 40*f*-1, 40*f*-2 and 40*f*-3 are stacked, for example. The image sensors 40*f*-1, 40*f*-2 and 40*f*-3 may be stacked in a direction parallel to the Z-axis in the CT system (e.g., a direction in which a patient or object being analyzed by the CT system is moved during analysis in a CT system), according to at least some example embodiments. Electrical communications between the dies of the image sensors 40*f*-1, 40*f*-2 and 40*f*-3 may be achieved by the TSV structures. Each image sensor, among image sensors 40*f*-1, 40*f*-2 and 40*f*-3, may have different optical or electrical characteristics such that a CT system using image sensors 40*f*-1, 40*f*-2 and 40*f*-3 can gather respectively different optical information from image sensors 40*f*-1, 40*f*-2 and 40*f*-3. Each image sensor among image sensors 40*f*-1, 40*f*-2 and 40*f*-3 may have different spectral characteristics against an incident light, or different spatial resolution which is inversely proportional to light sensitivity, for example. With the configuration described above with respect to FIG. 6(*b*), in addition to the above advantageous effects, a CT system, according to the embodiment, may have a hybrid imaging capabilities which enable multi-diagnoses using different light sources like different energy X-rays and/or NIR lights of multiple wavelengths, for example. According to at least some example embodiments, some or all of the stacked image sensors 40*f*-1, 40*f*-2, and 40*f*-3 of the sensor module 210 may be implemented by image sensors having the structure of the image sensor 40*d* illustrated in FIG. 5(*a*) and/or image sensors having the structure of the image sensor 40*e* illustrated in FIG. 5(*b*). According to at least some example embodiments, image sensor module 220 described in greater detail below with reference to FIG. 7(*a*) is an example of the manner in which image sensors 40*f*-1, 40*f*-2, and 40*f*-3 of the image sensor module 210 may be stacked.

Figure 4:
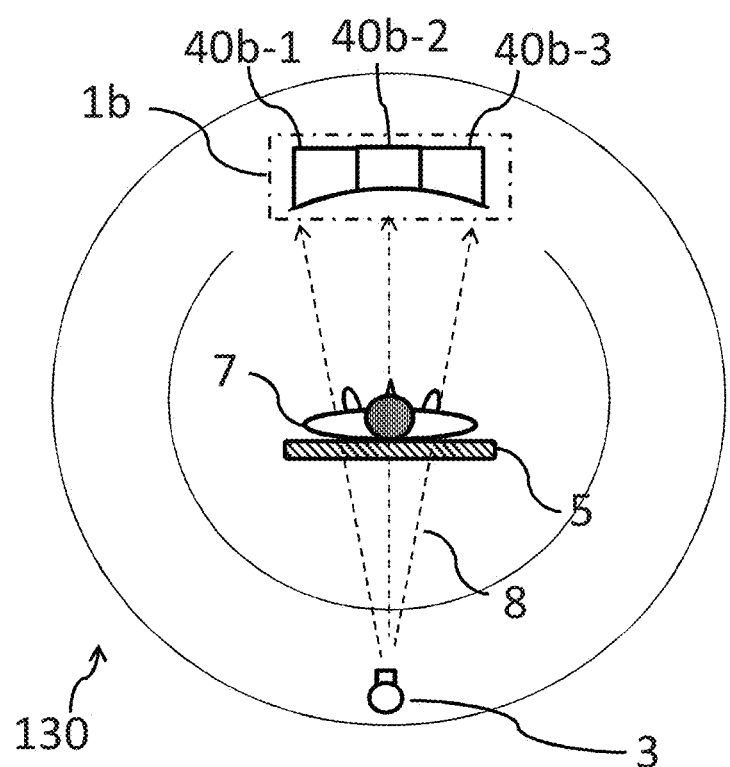
FIG. 4(a) is a diagram illustrating a plan view of a CT system with a view direction parallel to the Z-axis according to at least one example embodiment.
FIG. 4(b) is a diagram illustrating a plan view of a CT system with a view direction parallel to the Z-axis according to at least one example embodiment.
FIG. 4(c) is a perspective view of a CT system according to at least one example embodiment.
Figure 4:
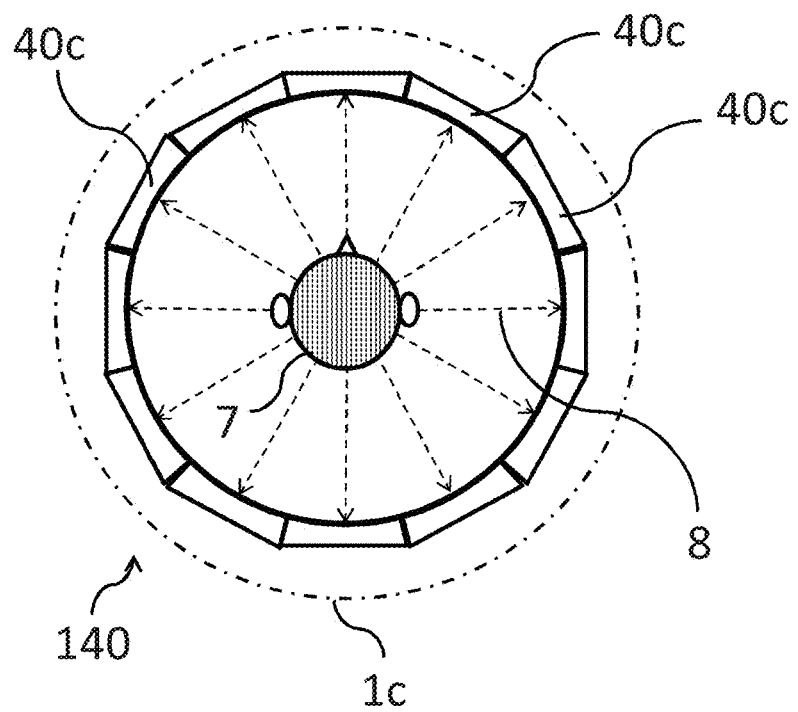
Figure 4:
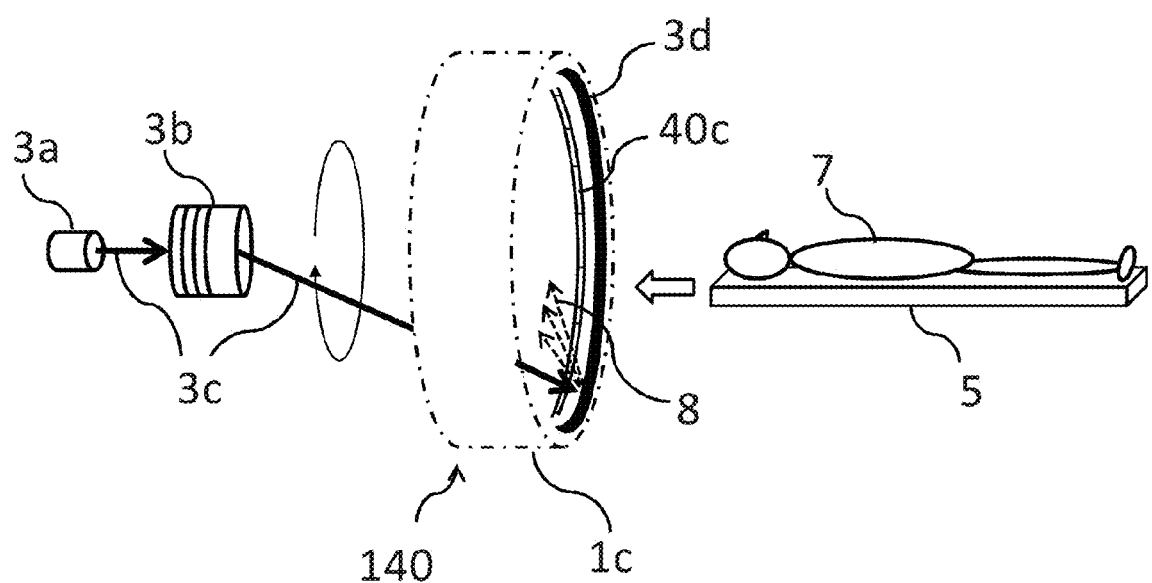
Figure 5:
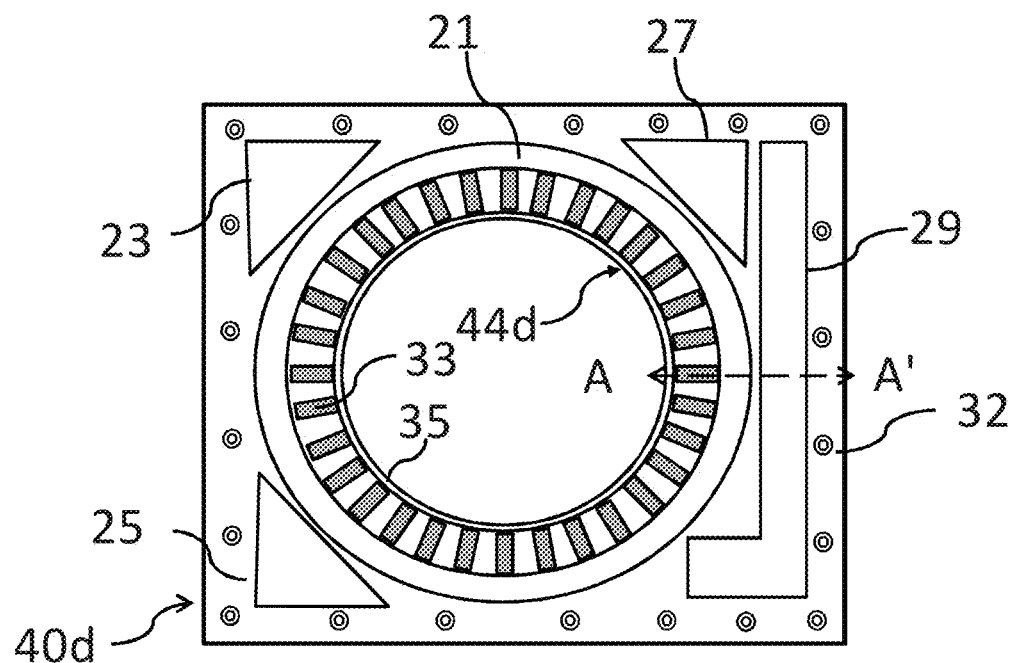
FIG. 5(a) is a diagram illustrating a plan view and a block diagram of an image sensor used in the CT system according to at least one example embodiment.
FIG. 5(b) is a diagram illustrating a plan view and a block diagram of an image sensor used in the CT system according to at least one example embodiment.
Figure 5:
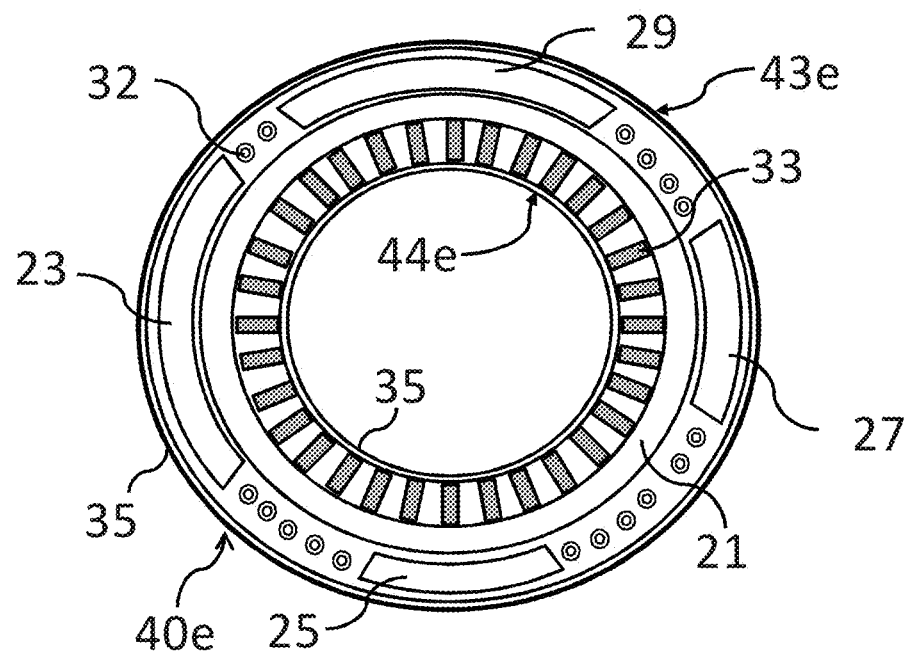

According to at least one example embodiment, the image sensors 40*f*-1-3 may be included in an imaging unit of a CT system in a manner that is the same as (or similar to) that discussed above with respect to the circularly-arranged image sensors 40*c* included in the imaging unit 1*c* of CT system 140 illustrated in FIG. 4(*c*). For example, according to at least some example embodiments, a CT system including the image sensors 40*f*-1-3 may include the electron beam gun 3*a*, focusing and deflection coil 3*b*, and target ring 3*d*, each of which may have the same arrangement and operation as those discussed above with respect to FIG. 4(*c*). Accordingly, X-rays beams generated as a result of an electron beam (e.g., electron beam 3*c*) irradiating the target ring 3*d* may be incident on an object located in the hollow center of the image sensors 40*f*-1-3, and resulting light that passes through or from the object may be incident on pixels located on the curved faces of the image sensors 40*f*-1-3.

According to at least some example embodiments, the implementation of portable CT systems may be facilitated when using image sensors like the image sensors 40*c*, 40*d*, 40*e*, and 40*f*-1-3 of FIGS. 4(*b*), 4(*c*), 5(*a*), 5(*b*), and 6(*b*), due to the relative ease with which a target ring (e.g., target ring 3*d*) can be attached to the flat, or alternatively, relatively flat faces of the image sensors 40*c*, 40*d*, 40*e* and 40*f*-1-3 (e.g., the flat faces, surfaces of which are perpendicular to a central axis of the hollow cylindrical spaces at the centers of the image sensors 40*c*, 40*d*, 40*e*, and 40*f*-1-3).

Figure 8:
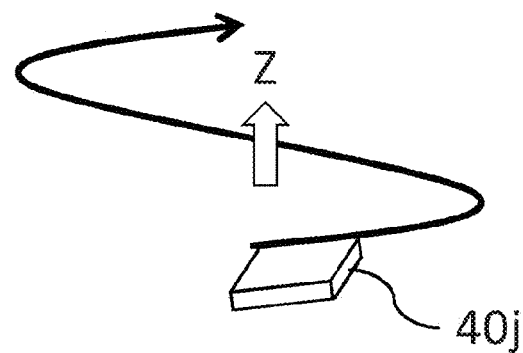
FIG. 8(a) is a diagram illustrating a perspective view of a helical path along which an image sensor moves when traveling around an object being analyzed by a CT system including the image sensor, according to at least one example embodiment.
FIG. 8(b) is a diagram illustrating a plan view and a block diagram of an image sensor used in the CT system according to at least one example embodiment, where the image sensor has a gap.
FIG. 8(c) is a diagram illustrating a cross sectional view of an imaging unit used in the CT system according to at least one example embodiment.
Figure 8:
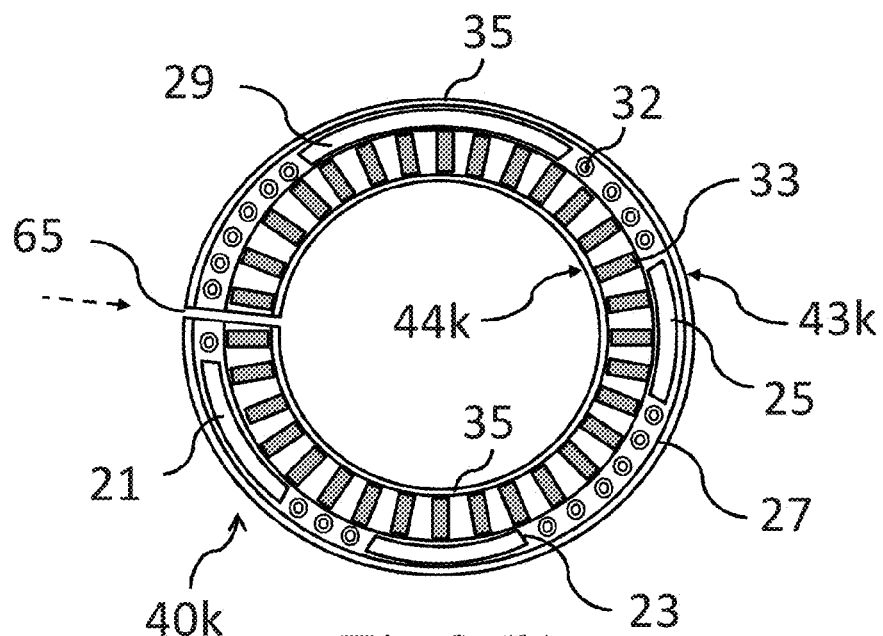
Figure 8:
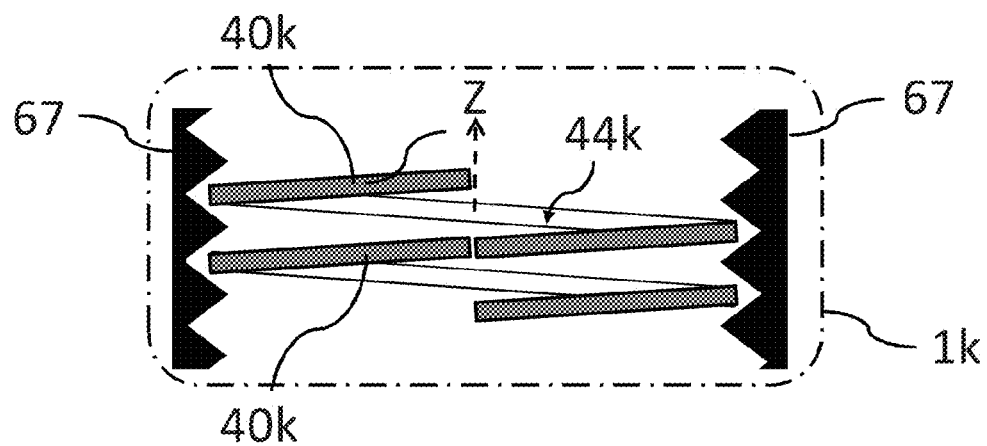

FIG. 7(*a*) is a diagram illustrating cross sectional views of an image sensor module 220 used in a CT system with respect to the X-Z plane and the Y-Z plane, according to at least one example embodiment. As is illustrated in FIG. 7(*a*), the image sensor module 220 may include a plurality of image sensors 40*g* stacked on each other. In the example shown in FIG. 7(*a*), the plurality of image sensors 40*g* includes three image sensors 40*g*-1, 40*g*-2, and 40*g*-3 are stacked in a direction parallel to the Z-axis to form an image sensor module 220. According to at least some example embodiments, each of image sensors 40*g*-1, 40*g*-2, and 40*g*-3 of the image sensor module 220 may have the structure of one of image sensors 40*a*, 40*b*, 40*c*, 40*d*, 40*e* discussed above, or image sensors 40*k* or 40*m* which will be discussed in greater detail below with reference to FIGS. 8(*b*) and 10(*b*). The left hand side and right hand side of FIG. 7(*a*) show cross sectional views with respect to a view direction parallel to the Y-axis and a view direction parallel to the X-axis, respectively. As shown in the left hand side of FIG. 7(*a*), pixels 20 form a pixel array two dimensionally in the X-Z plane. As shown in the right hand side of FIG. 7(*a*), image sensor 40*g*-2 is stacked on image sensor 40*g*-1 on which a non-conductive interlayer 53 is coated. Similarly, the image sensor 40*g*-3 is stacked on image sensor 40*g*-2 on which a non-conductive interlayer 53 is coated. TSVs 51 are formed in each image sensor 40*g*-1,40*g*-2, and 40*g*-3, in which conductive materials like aluminum, copper or doped poly-silicon, for example, may be embedded. Between each substrate (e.g., each silicon substrate of each silicon die of image sensors 40*g*-1, 40*g*-2, and 40*g*-3), micro bumps 55 are sandwiched to connect neighboring TSVs 51 electrically. According to at least some example embodiments, micro-pads 32 (not shown in this figure) may be inserted between the TSVs 51 and the micro-bumps 55.

It should be noted that, according to at least some example embodiments, the distances between the pixels 20 horizontally and vertically may be chosen so as to achieve desirable levels of quality for reconstructed images generated by a CT system including image sensor module 220. According to at least some example embodiments, the horizontal distance Dh may be determined by a fine micro fabrication technology like a photo-lithographic process with the highest accuracy. The vertical distance Dv may depend on the thickness Dt of the silicon substrate of one or more of image sensors 40g-1, 40g-2, and 40g-3 and the thickness of the non-conductive interlayer 53. The silicon substrate thickness Dt may be controlled and determined by a chemical and mechanical polishing (CMP) process applied to the backsides of the silicon wafers upon which the dies of image sensors 40g-1, 40g-2, and 40g-3 are created with an accuracy of 0.1 micron meter or less, for example. The thickness of the non-conductive interlayer 53 may be accurately controlled and determined by a chemical vapor deposition (CVD) technique during the image sensor manufacturing process with an accuracy of 0.1 micron meter or less, for example. There are at least two approaches to determine the values of the horizontal distance Dh and vertical distance Dv, respectively. With respect to the first approach, assuming a value of the horizontal distance Dh is fixed, the silicon substrate thickness Dt may be controlled by a CMP process to meet the requirement of the horizontal distance Dh being equal to vertical distance Dv, for example. According to at least one example embodiment, the horizontal distance Dh may be larger than the substrate thickness Dt. Using the CMP, the substrate thickness Dt may be thinned accurately down to 100 to several microns taking into account of the thickness of the non-conductive interlayer 53. With respect to the second approach, assuming a value of the vertical distance Dv is fixed, the horizontal distance Dh may be determined by a photo-mask pattern to meet the requirement of horizontal distance Dh being equal to the vertical distance Dv, for example. Unlike at least some conventional CT systems that combine multiple image sensors mechanically, where the distance between the pixels inside an individual image sensor may be different from the distance of between adjacent one of the multiple image sensors in the X-Y plane. With such a configuration, in addition to the above advantageous effects, a high spatial resolution with an accuracy of 0.1 micron or less for example, in directions parallel to the X, Y, and Z-axis can be realized, and then a capillary vessel or a brain tissue images, for example, may be clearly reconstructed by a relatively smaller-sized CT system.

According to at least some example embodiments, an area of each pixel 20 may be 100 (10 μm by 10 μm) to 10000 (100 μm by 100 μm) μm², for example. In the discussion of FIG. 7(a) above, according to at least some example embodiments, the vertical distance Dv is discussed as being equal to the horizontal distance Dh. Alternatively, the vertical distance Dv and horizontal distance Dh may be substantially equal to each other. According to at least some example embodiments, "substantially equal" refers to a difference between the vertical distance Dv and horizontal distance Dh that is, for example, less than 2 microns or less than 1 micron. According to at least some example embodiments, "substantially equal" refers to a difference between the vertical distance Dv and horizontal distance Dh that is, for example, no more than 0.02 microns or no more than 0.01 microns.

FIG. 7(b) is a diagram illustrating cross sectional views of an image sensor module 230 used in a CT system with respect to the X-Z plane, according to at least one example embodiment. Three image sensors 40h are stacked in the direction parallel to the Z-axis, and metal optical shields 57 are inserted between each adjacent pair of stacked sensors 40g to form the image sensor module 230. According to at least one example embodiment, each metal optical shield 57 may be composed of one or more materials, examples of which include, but are not limited to, metals including heavier metal atoms like tungsten or lead, in order to attenuate unexpected incident light with wrong directions or scattered X-ray beams. With such a configuration, in addition to the above advantageous effects, even higher image qualities of less cross-talk noise and artifact, for example, may be obtained. By inserting metal shield layers 57 between the image sensors 40g in the manner described above, the temperature of the image sensor module 230 may be kept lower in comparison to an image sensor module that does not include the metal shield layers in-between adjacent stacked image sensors, because the inserted metal shield layer may effectively release the heat generated inside the stacked image sensors 40g of the image sensor module 230, which may reduce a dark noise and improve a signal to noise ratio (S/N), thus allowing for even lower X-ray doses for an object or a patient being analyzed by a CT system including the image sensor module 230. According to at least some example embodiments, each of the image sensors 40h of the image sensor module 230 may have the structure of one of image sensors 40a, 40b, 40c, 40d, 40e discussed above, or image sensors 40k or 40m which will be discussed in greater detail below with reference to FIGS. 8(b) and 10(b).

FIG. 7(c) is a diagram illustrating a side view of the image sensor module 240 used in a CT system, according to at least one example embodiment. As is illustrated in FIG. 7(c), the image sensor module 240 includes four image sensors 40-4, 40-5, 40-6 and 40-7 stacked successively in a direction parallel to the Z-axis. As shown in FIG. 7(c), incident x-ray beam 8 reaches upper faces of the image sensors 40-4, 40-5, 40-6 and 40-7. In the example illustrated in FIG. 7(c), a color filter 59, which selectively transmits or blocks a certain range of light wavelengths to improve image quality like sharpness or energy resolutions, is laminated on the top of image sensor 40-4, for example. In the example illustrated in FIG. 7(c), nothing, except a surface thin silicon dioxide layer and a thin impurity doped layer (neither of which is illustrated in FIG. 7(c)), is laminated on the top of image sensor 40-5, which may detect incident beams like a soft X-ray or an alpha-ray, for example. In the example illustrated in FIG. 7(c), a near-infrared (NIR) filter 61, which selectively transmits NIR light and blocks visible light from the surroundings to improve spectral resolutions, is laminated on the top of image sensor 40-6, for example. In the example illustrated in FIG. 7(c), a scintillator 63, which may effectively convert an incident X-rays to visible light of a known wavelength, is laminated on the top of image sensor 40-7. According to at least one example embodiment, the scintillator 63 is embodied by an organic scintillator like anthracene or stilbene, for example, which may be laminated on the image sensor by a known coating and etching process. According to at least some example embodiments, X-rays, which penetrate through the scintillator 63 without emitting a light, may be also detected by the image sensor 40-7 as explained above.

With the configuration described above with reference to FIG. 7(b), in addition to the above advantageous effects, a CT system using the image sensor module 240, according to at least some example embodiments, may have a hybrid imaging capabilities which enable multi-diagnosis capabilities by using different light sources like different energy X-rays and/or NIR lights of multiple wavelengths, for example.

FIG. 8(a) is a diagram illustrating a schematic drawing of an image sensor arrangement inside an imaging unit of a CT system. An image sensor 40j is placed along the trace of a helix extending in the direction of Z-axis as indicated an arrow of solid line which does not exist but is just for explanation. For example, the imagining unit in which the image sensor 40j is included may be structured such that the image sensor 40j follows the helical path illustrated by the solid arrow illustrated in FIG. 8(a). As is illustrated in FIG. 8(a), at least one face of the image sensor 40j may face a center of the helical path. The face of the image sensor 40j that faces the center of the helical path may have a modified concave in shape and some mechanical deformation. According to at least one example embodiment, more than two image sensors 40j may be located approximately along the helix. With such a configuration, according to the embodiment, CT system may have advantageous effects of both helical and multi-scan system capable of a high speed imaging and a low radiation exposure. The spatial resolution in the direction of Z-axis may be improved when a moving speed of an object being analyzed by a CT system in which the image sensor 40j is included with respect to a direction parallel to the Z-axis is equal to the moving speed of the image sensor 40j in the direction parallel to the Z-axis while an imaging unit in which the image sensor 40j is included (not illustrated in FIG. 8(a)) is rotating around the object.

FIG. 8(b) is a diagram illustrating a plan view of an image sensor 40k which, according to at least some example embodiments, may provide at least some benefits over helix structures used in imaging units of at least some CT systems. The photo-diodes 33, peripheral circuits 21, 23, 25, 27, 29 and micro-pads 33 may be formed on a single die, for example, in the same manner discussed above with respect to image sensor 40e of FIG. 5(b). According to at least some example embodiments, the image sensor 40k may have the same structure as that described above with respect to the image sensor 40e, with the exception that the silicon substrate of the silicon die of the image sensor 44e includes a slit or gap 65. The slit 65 may facilitate deformation the image sensor 40e into the shape of a helix or a section of a helix, for example. As is explained above with reference to the image sensor 40e, both outer and inner faces 43k and 44k of the silicon substrate of the image sensor 40k may be covered (e.g., coated) by thin silicon dioxide layers 35. The inner face 44k does not form a closed circle but may form a part of helix around an object located in a region central to the helical shape formed by the image sensor 40k FIG. 8(c) is a diagram illustrating a side view of two stacked image sensor 40k engaged with edges of a holding member 67 inside an imaging unit 1k. In the example shown in FIG. 8(c), the image sensors 40k shown in FIG. 8(b) are stacked on each other and, together, form the shape of a helix that extends in a direction parallel to the Z-axis. The holding member 67 may be a structure formed such that interior edges of the holding member 67 have a shape of screw threads inside the cylindrical tube. The screw-thread-shaped edges of the holding member 67 may be shaped so as to mesh with edges of the helix-shaped image sensors 40k, in the manner shown in FIG. 8(c). According to at least some example embodiments, the relationship between the stacked image sensors 40k and the holding member 67 is like that of screw and nut. With the configuration described above with reference to FIG. 8(c), according to at least some example embodiments, an image sensor 40k or a plurality of image sensors 40k stacked together may be are accurately fixed in a helical shape inside the imaging unit 1k, and may be replaced with a new image sensor easily. As is shown in FIG. 8(c), the image sensor 40k may have a shape of a helix that winds in such a manner as to define a cylindrical space about which the helix is wound. Further, the curved face 44k may face the cylindrical space such that an array of pixels 20 formed on the curved face 44k may face an object located in a central portion of the cylindrical space and receive light that travels through or from the object located in a central portion of the cylindrical space. According to at least one example embodiment, the image sensor 40k may be included in an imaging unit of a CT system in a manner that is similar to that discussed above with respect to the circularly-arranged image sensors 40c included in the imaging unit 1c of CT system 140 illustrated in FIG. 4(c). For example, according to at least some example embodiments, the imaging unit 1k may include the target ring 3d. Further, a CT system including the imaging unit 1k may include the electron beam gun 3a and focusing and deflection coil 3b. The electron beam gun 3a, focusing and deflection coil 3b and target ring 3d may each have the same arrangement and operation as those discussed above with respect to FIG. 4(c). Accordingly, X-rays beams generated as a result of an electron beam (e.g., electron beam 3c) irradiating the target ring 3d may be incident on an object located in the hollow cylindrical center of the helical image sensors 40k, and resulting light that passes through or from the object may be incident on pixels located on the curved faces 44k of the helical image sensors 40k of the imaging unit 1k.

Figure 9:
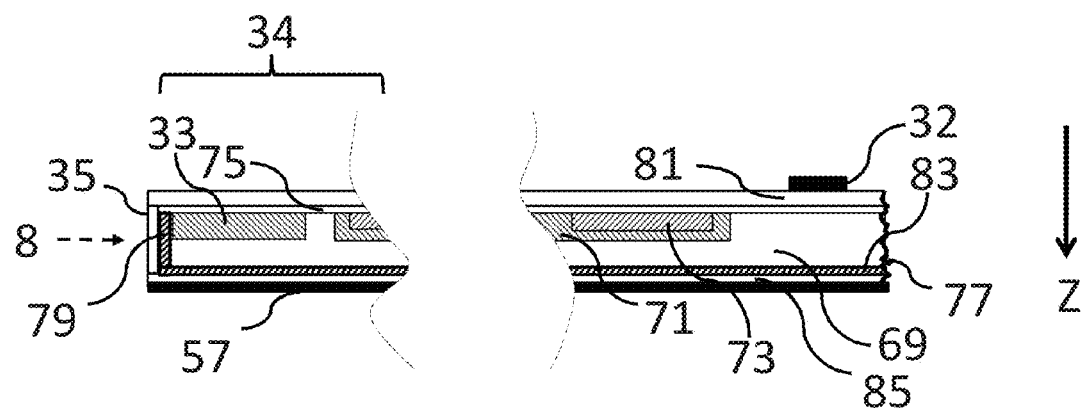
FIG. 9(a) is a diagram illustrating a cross sectional view of an image sensor used in the CT system according to at least one example embodiment.
FIG. 9(b) is a diagram illustrating an enlarged portion of the cross sectional view of the photo-electrical conversion region illustrated in FIG. 9(a), according to at least one example embodiment.
Figure 9:
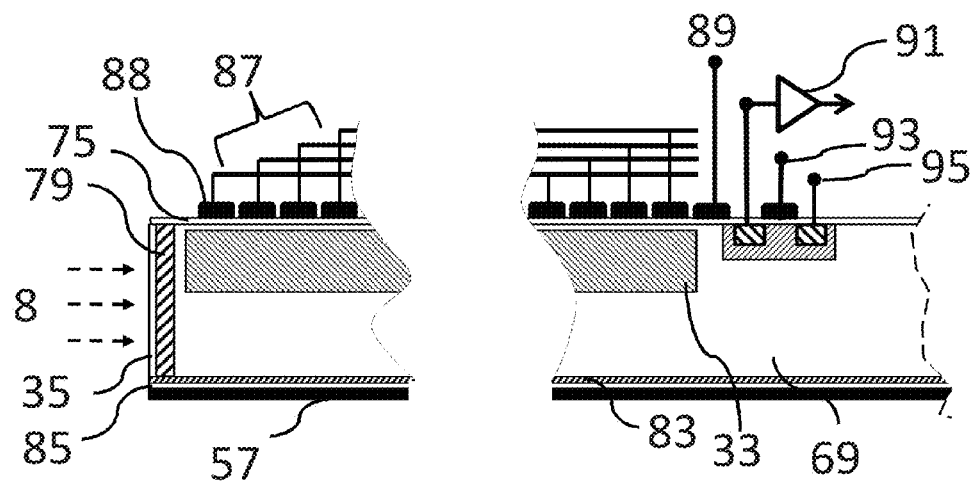

FIG. 9(a) is a diagram illustrating a cross sectional view taken along a dotted line A-A' of the image sensor 40d shown in FIG. 5(a) according to at least one example embodiment. An X-ray beam 8, illustrated as entering from a left side of FIG. 9(a), for example, may irradiate a face of a silicon substrate 69. According to at least some example embodiments, the silicon substrate 69 may be a p-type silicon substrate. The X-ray beam 8 penetrates into a photo-diode 33. The photo-diode 33 may be fully depleted inside the silicon substrate 69. The X-ray beam 8 that penetrates into the photo-diode 33 may be read out in a photo-electrical conversion region 34. As will be discussed in greater detail below with reference to FIG. 9(b), the photo-electrical conversion region may include the photo-diode 33 and a floating gate amplifier 91. The silicon dioxide layer 35, which may be thermally grown in an oxidizing atmosphere, is formed on the face of the substrate 69 upon which the X-ray beam 8 may be incident. On the p-type substrate 69, n-well 71 is formed, and p-well 73 is formed on the n-well 71, where CMOS peripheral circuits may be formed. According to at least some example embodiments, the silicon substrate 69 is covered by a thin gate silicon dioxide 75 and thick nonconductive layer 81. The backside of the substrate 69 may have a thin $P^+$ doped region 83 adjacent to a thin silicon dioxide layer 85. According to at least some example embodiments, a thin $P^+$ doped region 79 is located between the thin silicon dioxide layer 35 and the photo-diode 33. The thin $P^+$ doped region 79 and the thin silicon dioxide layer 35 may prevent crystal defects and impurity contaminations. A metal optical shield 57 including, for example, tungsten atoms, is laminated on the backside of the substrate 69. The advantageous effects of the metal optical shield 57 are already mentioned above with reference to FIG. 7(b). A face of the substrate 59 near the micro-pad 32 may have a rough surface 77 which may be caused by a dicing saw, for example. The n-well 71 and the p-well 73, where peripheral circuits may be formed, are separated from the rough surface 77 such that the micro pad 32 is between the rough surface 77 and n-well 71/p-well 73. With such a configuration, a conventional dicing saw may be used for the wafer dicing process without degrading the sensor characteristics caused by crystal defects or mechanical stress.

FIG. 9(b) is a diagram illustrating an enlarged portion of the photo-electrical conversion region 34 illustrated in FIG. 9(a). The photo-diode 33 may include an n-type impurity region on the silicon substrate 69 and may extend in a direction parallel to a longer side of the silicon substrate 69 as illustrated in FIGS. 9(a) and 9(b) (i.e., a direction parallel to incident beam 8 or perpendicular to the Z-axis). The length of the photo-diode 33 in the direction parallel to the longer side of the silicon substrate 69 may have a range of one micron to ten millimeters, for example, which effectively enables photo-detections of infrared light and/or X-rays, for example. Further, according to at least some example embodiments, the photo-diode 33 including an n-type impurity region on the silicon substrate 69 may also extend radially toward the incident beam 8 in the X-Y plan view as shown in FIGS. 5(a), 5(b) and 8(b), for example. According to at least some example embodiments, the photo-diode 33 illustrated in FIG. 9(b) may be one of a plurality of photo-diodes, and may be electrically separated from neighboring photo-diodes by a device isolation region including a highly $P^+$ doped region (not illustrated in FIG. 9(a) or FIG. 9(b)), for example. A wiring group of four-phase driving pulses 87 may be formed above the photo-diode 33 in order to transfer generated charges toward a floating gate amplifier 91 in a manner that is the same as or, alternatively, similar to, known CCD image sensor operations. In the example shown in FIG. 9(b), the charge transfer gate electrodes 88 are formed on the thin gate silicon dioxide layer 75 in a direction parallel to the incident beam 8. Conventional CCD or MOS image sensors, at least some of which require a thick silicon substrate of more than 500 micron-meters to detect incident lights like X-rays in the direction parallel to the incident X-rays, may need a high voltage of more than 100 volts or higher in order to deplete the silicon substrate almost down to the bottom of the substrate. Moreover, unlike conventional CCD or MOS image sensors, in the image sensor structures shown FIGS. 9(a) and 9(b) neither an electrode nor a transistor (either of which may attenuate the incident light 8), exists in the optical path through which the incident light 8 travels to reach the photodiode 33. According to at least some example embodiments, only the thin $P^+$ doped region 79 and/or the thin silicon dioxide layer 35 are located along the optical path through which the incident light 8 travels to reach the photodiode 33. As a result, an image sensor that has a higher sensitivity, has less variation, and generates fewer false signals (e.g., artifacts) may be obtained. The detection efficiency of an incident light may depend on the light energy and the distance that the light traveled through the silicon substrate in the direction parallel to a direction in which the array of the charge transfer gate electrodes 88 are arranged as shown in FIG. 9(b). When operating in a CCD mode, for example, each charge packet data has information on each position above an array of photo-diode 33, and thus, it may become possible to analyze the incident light energy as a function of the position or the distance from the side of the image sensor.

Initially, the electric potential of the floating gate may be reset to that of the reset drain 95 by switching the reset gate 93 (e.g., by allowing charge carriers to flow through a channel of the reset gate 93, which may be an MOSFET). Light exposure may start immediately after the photo-diode 33 is fully depleted by the four-phase driving pulses 87. Electric charges generated and collected in each packet may be transferred toward the floating gate amplifier 91, and finally the collected charges are read out into the floating gate of the floating gate amplifier 91 by switching the signal read-out gate 89 (e.g., by allowing charge carriers to flow through a channel of the read-out gate 89, which may be a MOSFET). With such the configuration described above with reference to FIG. 9(b), the photo-diode 33 may be fully depleted along the incident light path without using a thick silicon substrate of more than 200 micron meters, and without applying a high voltage of more than 20 volts, for example.

FIG. 10(a) is a diagram illustrating a plan view and a block diagram of an image sensor 40m used in the CT system according to at least one example embodiment. Similar to the configuration of the image sensor 40a illustrated in FIG. 3(a), peripheral circuits 21, 23, 25, 27, 29 are located between an array of photo-diodes 33 and micro-pads 32. The micro-pads 32 may be used in stacked sensor structure. The face of the sensor 40m being exposed to an incident light may be concave in shape like concave face 44a of image sensor 40a illustrated in FIG. 3(a). As is illustrated in FIG. 10(a), the photo-diodes 33 of the image sensor 40m may be formed radially in a fan-shaped array to detect radial incident lights. According to at least one example embodiment, the photo-diodes 33 of the image sensor 40m each extend from the curved face of the image sensor 40m into the image sensor in a direction parallel to a direction in which a beam of light traveling in a straight line from an X-ray source to the photo-diode would travel. The circuit blocks 37 and 39 may be an on chip buffer memory and a data compression circuit, respectively. With the configuration discussed above with reference to FIG. 10(a), the image data after analog to digital conversion by the circuit block 25 may be compressed down to size between one third and one fifth of an original size of the image data without data loss, for example, and thus the data transfer bit rate may be decreased.

FIG. 10(b) is a diagram illustrating a perspective view of an image sensor module used in the CT system according to at least one example embodiment. Similar to the configuration of the image sensor module 200 illustrated in FIG. 6(a), the image sensor module 250 includes three image sensors 40m as shown in FIG. 10(a), for example. In addition, an image processing chip 45 is stacked on the top of the uppermost image sensor 40m of the image sensor module 250. Between the image processing chip 45 and the uppermost image sensor 40m, micro-pads and micro-bumps (neither of which are illustrated) may be formed to enable electrical communication each other. Though, FIG. 10(b) is illustrates image sensor module 250 as including the processing chip 45 stacked atop a plurality of image sensors 40m of FIG. 10(a) stacked on each other, according to at least some example embodiments, the image sensor module 250 may include the processing chip 45 stacked atop a plurality of image sensors 40a of FIG. 3(a) stacked on each other.

FIG. 10(c) is a diagram illustrating a block diagram of the image processing chip 45 according to at least one example embodiment. A signal control circuit 11, a multiplexer circuit 12, a data buffer circuit 13 and a parallel to serial converter circuit 14 are formed on the image processing chip 45, for example.

Figure 10:
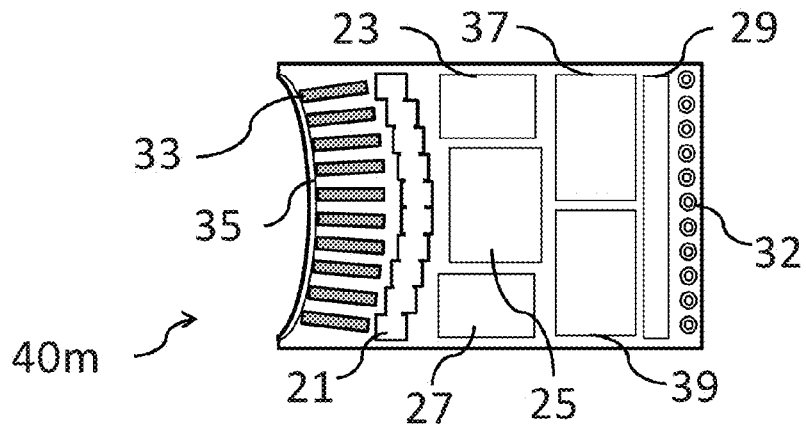
FIG. 10(a) is a diagram illustrating a plan view and a block diagram of an image sensor used in the CT system according to at least one example embodiment.
FIG. 10(b) is a diagram illustrating a perspective view of an image sensor module used in the CT system according to at least one example embodiment.
FIG. 10(c) is a diagram illustrating a block diagram of an image processing chip stacked on the image sensor used in the CT system according to at least one example embodiment.
FIG. 10(d) is a diagram illustrating a plan view of an imaging unit and an image processing unit used in the CT system according to at least one example embodiment.
Figure 10:
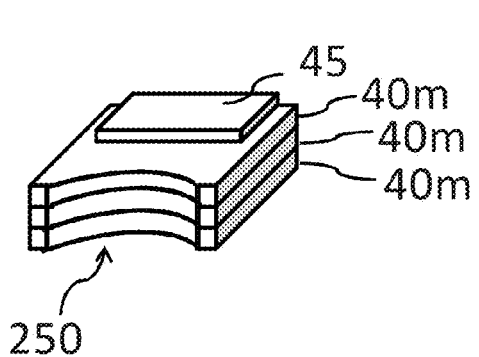
Figure 10:
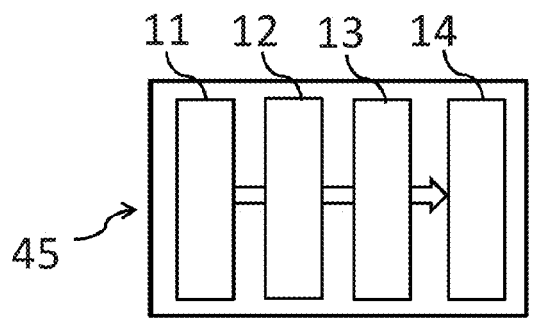
Figure 10:
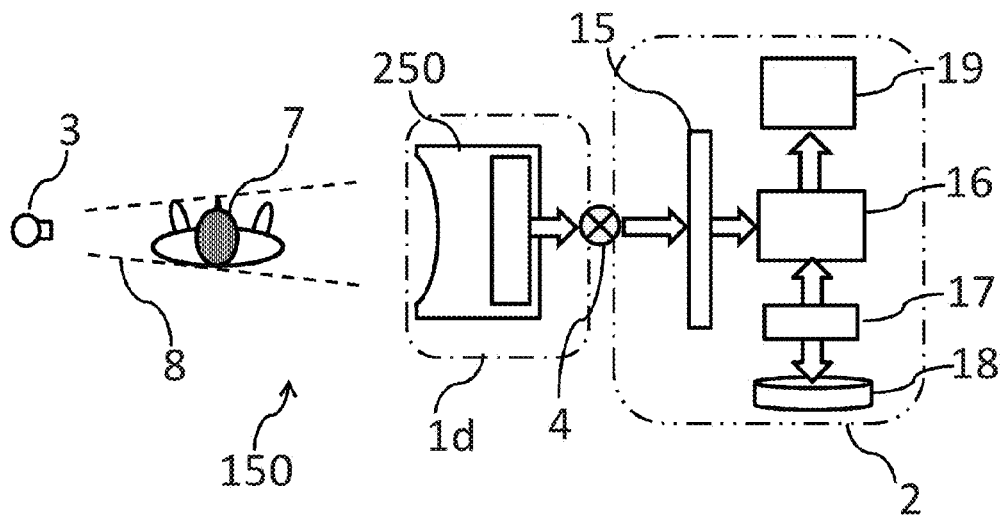

FIG. 10(d) is a diagram illustrating a plan view of an imaging unit 1d including the image sensor module 250 of FIG. 10(b), and an image processing unit 2 used in the CT system 150 according to at least one example embodiment. The CT system 150 also includes an X-ray source 3, and an object or patient 7. The X-ray fan beam 8 may be collimated by a collimator (not illustrated) to form a defined fan beam angle (not illustrated), for example. The X-ray source 3 projects an X-ray fan beam 8, for example, through the object 7 to be detected by the image sensor module 250. The imaging unit 1*d* and the X-ray source 3 are located in an opposite position inside a gantry. The gantry rotates around the object 7 taking a slice image, and the object is moved in a direction parallel to the Z-axis in order to allow the CT system 150 to obtain additional slice images. The semiconductor surface of the image sensor module 250, where integrated circuits are formed, may be perpendicular to the Z axis. As FIGS. 10(*d*) and 10(*b*) illustrate, the image sensor module 250 may include a concave face. The concave face of the image sensor module 250 may face an object 7 in order to detect incident X-ray fan beam 8. The imaging unit 1*d* including the image sensor module 250 which outputs compressed digital image data may be electrically connected with the image processing unit 2 via the slip-ring 4, for example. When compressed image data is received through the slip-ring 4, a network interface circuit 15 may assign the received data to other circuit blocks such as a central processing unit (CPU) 16 which may perform a reconstruction of a slice image, for example. Either raw or processed image data may be read or written to or from a memory disk unit 18 by a disk controller circuit 17. Image data with other related information may be monitored by, for example, a doctor via an image output device 19 such as a LCD screen. With the configuration described above with respect to FIG. 10(*d*), compressed image data obtained from the stacked image sensors may be directly sent to the upper image processing chip 45 using electrical paths (which may be reduced or, alternatively, minimized in terms of number and/or length) by TSVs and without discrete high speed line drivers or buffers between the chips. As a result, high speed data transfer and a data processing, and lower power consumption, relative to at least some conventional CT systems, may be achieved by the CT system 150. In example illustrated in FIG. 10(*d*), the circuit blocks 37 and 39 are integrated on each image sensor 40. According to at least some example embodiments, the circuit blocks 37 and 39 may be integrated on the upper image processing chip 45, which may allow die size and/or data management to be improved or, alternatively, optimized for each of the image sensors 40*m* of the image sensor module 250.

As is explained above, the CT systems according to at least some example embodiments enable the discovery of a disease or other conditions harmful to the health of a patient in the early stages, and as a result, reduce medical expenses. The CT systems according to at least some example embodiments may provide not only increased sensitivity, lower X-ray dose to patients being analyzed by the CT systems and increased image quality, but also a high data transfer rate with low power consumption, small or portable form factor, reduced maintenance load, and a lower amount of influence by environmental factors experienced by the CT systems like temperature, humidity and mechanical vibrations are obtained. In addition, the CT system according to at least some example embodiments provide high spatial, time and energy resolution enabling three dimensional (3D) imaging with a variety of valuable biomedical information on carcinoma tissue and capillary vessels around a beating heart, for example.

Though example embodiments of CT systems are described above in the context of medical image systems, the CT systems according to at least some example embodiments are not limited to medical applications, and may also be suitable for applications including X-ray phase shift imaging using, for example, a micro-focused X-ray source, various industrial X-ray imaging systems, X-ray astronomy, and high energy physics applications.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed:
1. A tomographic imaging system comprising:
    a source configured to irradiate an object;
    a first image sensor including a first semiconductor substrate having a first face upon which a monolithic first pixel array is located; and
    a gantry configured to hold the first image sensor and rotate the first image sensor around the object about a first rotation axis,
    the first pixel array including a first plurality of pixels configured to receive light that travels through or from the object based on the irradiation,
    the first plurality of pixels of the first pixel array being arranged in one or more rows and a plurality of columns such that,
        a total number of the one or more rows is less than a total number of the plurality of columns, and
        the one or more rows extend in a first direction,
    the first image sensor being arranged such that tilt angle between the first direction and a second direction is greater than 45 degrees and equal to or less than 90 degrees,
    the second direction being a direction parallel to the first rotation axis or a direction in which the object moves during analysis of the object by the imaging system.
2. The tomographic imaging system of claim 1, further comprising:
    one or more peripheral circuits,
    the one or more peripheral circuits including at least one of a signal read-out and scanning circuit, a timing pulse generator circuit, an analog-to-digital converter (ADC) circuit, a digital signal processing circuit, or an interface circuit,
    the one or more peripheral circuits being located at positions on the first semiconductor substrate that are spaced away from edges of the first image sensor.
3. The tomographic imaging system of claim 1, wherein the first face has a concave shape.
4. The tomographic imaging system of claim 3, wherein the first plurality of pixels include a plurality of photo-diodes, respectively.
5. The tomographic imaging system of claim 4, wherein the plurality of photo-diodes are arranged radially in the first image sensor such that, for each photo-diode of the plurality of photo-diodes,
    the photo-diode extends from the first face into the first image sensor in a direction parallel to a third direction, the third direction being a direction in which a beam of light traveling in a straight line from the source to the photo-diode would travel.
6. The tomographic image system of claim 3 further comprising:
    an image sensor module including the first image sensor and at least a second image sensor stacked on the first image sensor, the second image sensor including a second semiconductor substrate having a second face upon which a monolithic second pixel array is located,
the second pixel array including a second plurality of pixels configured to receive light that travels through or from the object based on the irradiation.

7. The tomographic image system of claim 6, wherein the second image sensor is stacked on the first image sensor such that a first distance is substantially equal to a second distance,
the first distance being a distance between a center of a first pixel and a center of a second pixel,
the second distance being a distance between a center of the first pixel and a center of a third pixel,
the first pixel and second pixels being pixels from among the first plurality of pixels,
the first and second pixels being adjacent to each other and both located in a same one of the one or more rows of the first pixel array,
the third pixel being a pixel from among the second plurality of pixels of the second pixel array.

8. The tomographic imaging system of claim 6, wherein the image sensor module includes a metal optical shield between the first and second image sensors.

9. The tomographic imaging system of claim 6, wherein the image sensor module includes an image processing chip stacked on the second image sensor.

10. The tomographic imaging system of claim 9, wherein the image sensor module includes one or more data compression circuits.

11. The tomographic imaging system of claim 1, wherein the first face is coated with a silicon dioxide layer.

12. The tomographic imaging system of claim 1, wherein the first image sensor is a single-die image sensor chip.

13. The tomographic imaging system of claim 12, wherein the image sensor chip includes an analog-to-digital converter (ADC) circuit.

14. The tomographic imaging system of claim 1 wherein the second direction is a direction parallel to the first rotation axis.

15. The tomographic imaging system of claim 1 wherein the second direction is a direction parallel to the direction in which the object moves during analysis of the object by the imaging system.

* * * * *